(12) United States Patent
Roseman et al.

(10) Patent No.: US 9,161,718 B2
(45) Date of Patent: *Oct. 20, 2015

(54) TREATMENT OF CEREBRAL PALSY IMPAIRED SPEECH IN CHILDREN

(71) Applicant: Gilrose Pharmaceuticals, LLC, White Plains, NY (US)

(72) Inventors: Bruce Roseman, White Plains, NY (US); Gilla Kaplan, New York, NY (US)

(73) Assignee: GILROSE PHARMACEUTICALS, LLC, White Plains, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/463,838

(22) Filed: Aug. 20, 2014

(65) Prior Publication Data
US 2014/0357668 A1 Dec. 4, 2014

Related U.S. Application Data

(60) Division of application No. 14/182,332, filed on Feb. 18, 2014, now abandoned, and a division of application No. 14/059,541, filed on Oct. 22, 2013, now Pat. No. 8,883,815, which is a continuation-in-part of application No. 14/112,065, filed as application No. PCT/US2012/038312 on May 17, 2012, now Pat. No. 9,089,563.

(60) Provisional application No. 61/487,847, filed on May 19, 2011.

(51) Int. Cl.
| | |
|---|---|
| A61K 31/435 | (2006.01) |
| A61K 31/135 | (2006.01) |
| A61B 5/00 | (2006.01) |
| A61K 31/137 | (2006.01) |
| A61K 31/4458 | (2006.01) |
| A61K 45/06 | (2006.01) |
| A61B 5/055 | (2006.01) |

(52) U.S. Cl.
CPC ............ *A61B 5/4803* (2013.01); *A61K 31/137* (2013.01); *A61K 31/4458* (2013.01); *A61K 45/06* (2013.01); *A61B 5/055* (2013.01); *A61B 5/4064* (2013.01)

(58) Field of Classification Search
CPC ............ A61K 31/4458; A61K 49/004; A61K 2121/00
USPC .................................. 514/277, 654
See application file for complete search history.

(56) References Cited

U.S. PATENT DOCUMENTS

| | | | |
|---|---|---|---|
| 5,213,553 | A | 5/1993 | Light |
| 6,121,261 | A | 9/2000 | Glatt et al. |
| 8,426,423 | B2 | 4/2013 | Jordan et al. |
| 8,883,815 | B2 | 11/2014 | Roseman |

| | | | |
|---|---|---|---|
| 2004/0092605 | A1 | 5/2004 | Jerussi et al. |
| 2006/0052428 | A1 | 3/2006 | Chez |
| 2006/0161218 | A1 | 7/2006 | Danilov |
| 2011/0178114 | A1 | 7/2011 | Aung-Din |

OTHER PUBLICATIONS

Pennington et al., Effects of It Takes Two to Talk, The Hanen Program for parents of preschool children with CP; Findings from an exploratory study; Journal of Speech, Language and Hearing Research 52, (5) 1121-1138 (2009).
WO 2012/158892 (Roseman et al.); Nov. 22, 2012; Abstract.
Reorganization after pre—and perinatal Brain Lesions; Martin Staudt; Journal of Anatomy; 2010; pp. 469-474.
New insights into the pathology of white matter tracts in cerebral palsy . . . ; Schecket al.;Developmental Medicine & Child Neurology; Mar. 2012; pp. 684-695.
Pharmacotherapy of Spasticity in Children with Cerebral Palsy; Verrotti et al; Elsevier, Inc. 2006; pp. 1-6.
Speech and Language Therapy for Children with Cerebral Palsy . . . US National Library of Medicine; Jul. 21, 2006; pp. 1-2.
Intensive Speech and Language Therapy for Older Children . . . Cerebral Palsy . . . ; Pennington et al.; Developmental Medicine & Child Neurology; Apr. 2009; pp. 337-344.
Dopamine Treatment in Children with Cerebral Palsy; Shaare Zedek Medical Center; NIH; May 2011; pp. 1-3.
Perceptual and Articulatory Changes in Speech Production . . . Maria I. Griogs, Ph.D., et al.; J. Med. Speech Language Pathol. 2012; 18(4); pp. 46-53
Speech Problems Affect More Than one in Two Children with Cerebral Palsy . . . A. Nordberg et al.; ACTA Paediatriaca; 2012; pp. 161-166.
Speech, Expressive Language, and Verbal Cognition . . . with Cerebral Palsy in Iceland; Development Medicine & Child Neurology; Jul. 2010; Solveig et al.; pp. 74-80.
Oromotor Variability in Children with Mild Spastic Cerebral Palsy . . . ; Journal of Neuroengineering and Rehabilitation; 2010; Chia-Ling Chen, et al.; pp. 1-10.
Oromotor Dysfunction and Communication Impairments in Children with Cerebral Palsy . . . ; Parkes, et al.; Developmental Medicine & Child Neurology; Jun. 2010; pp. 1113-1119.
Long-Term Survival for a Cohort of Adults with Cerebral Palsy; Hemming Ph.D., et al.; Developmental Medicine & Child Neurology; 2006; 48: pp. 90-95.
Development of the FOCUS, a Communication Outcome Measure for Preschool Children; Thomas-Stonell, et al. Developmental Medicine & Child Neurology; Jun. 2009; pp. 47-53.
Language and Motor Speech Skills in Children with Cerebral Palsy; Pirila, et al.; Journal of Communiation Disorders 40: (2007); pp. 116-128.

(Continued)

*Primary Examiner* — Kevin E Weddington
(74) *Attorney, Agent, or Firm* — Marvin Feldman; Lackenbach Siegel LLP

(57) ABSTRACT

Cerebral palsy impaired speech in children and adolescents are effectively treated by administration of a psychostimulant. Low doses of the psychostimulant significantly increases the percentage of correctly pronounced intelligible syllables or words and the ability to more intelligibly communicate. The improvement in speech persists after cessation of or prior to continued psychostimulant treatment.

24 Claims, 19 Drawing Sheets

(56) References Cited

OTHER PUBLICATIONS

Survival of Individuals with Cerebral Palsy Born in Victoria, Australia . . . ; Reid, et al.; Developmental Medicine & Child Neurology; Oct. 2011; pp. 353-360.

Factors Associated with Motor Speech Control in Children with Spastic Cerebral Palsy; Chia-Ling Chen, et al.; Chang Gung Medical Journal; vol. 33, No. 4; Jul.-Aug. 2010; pp. 415-423.

Intensive Speech and Language Therapy for Older Children with Cerebral Palsy: A Systems Approach; Penning, et al.; Developmental Medicine & Child Neurology; Apr. 2009; pp. 337-344.

Dysarthria Treatment; Chandramita Bora; Apr. 19, 2010; Buzzle; pp. 1-2.

Speech and Language Therapy for Children with CP might Improve their Communication Skills, but More Research is needed; PubMed Health/NIH; John Wiley & Sons, Ltd. pub. Jul. 21, 2003.

NINDS Cerebral Palsy Information Page; NIH National Institute of Neurological Disorders and Stroke . . . Aug. 21, 2013.

The Effect of Methylphenidate on the Verbal Productivity of Children with Cerebral Dysfunction; Ray O. Creager and Catharine Van Riper; J. Speech Hear Res. 1967:10;623-628.

Methylphenidate for Giggle Incontinence; Amanda K. Berry et all., The Journal of Urology; vol. 182; Issue 4; Supplement; pp. 2028-2032; Oct. 2009.

Methylphenidate for the Treatment of Gait Impairment in Parkinson's Disease; NIH Clinical Trials; pp. 1-5; Oct. 27, 2009.

PCT/US2012/028212 international search report and written opinion.

PCT publication WO 2012/158892 A2.

Effect of Amphetamines on Speech Defects in the Mentally Retarded; Charles H. Fish, MD, MPH and Evelyn Bowling; California Medicine, vol. 96, No. 2, Feb. 1962; pp. 109-111.

International Search Report PCT/US2014/060868, Dated Mar. 27, 2015.

Written Opinion, PCT/US2014/060868, Dated Mar. 27, 2015.

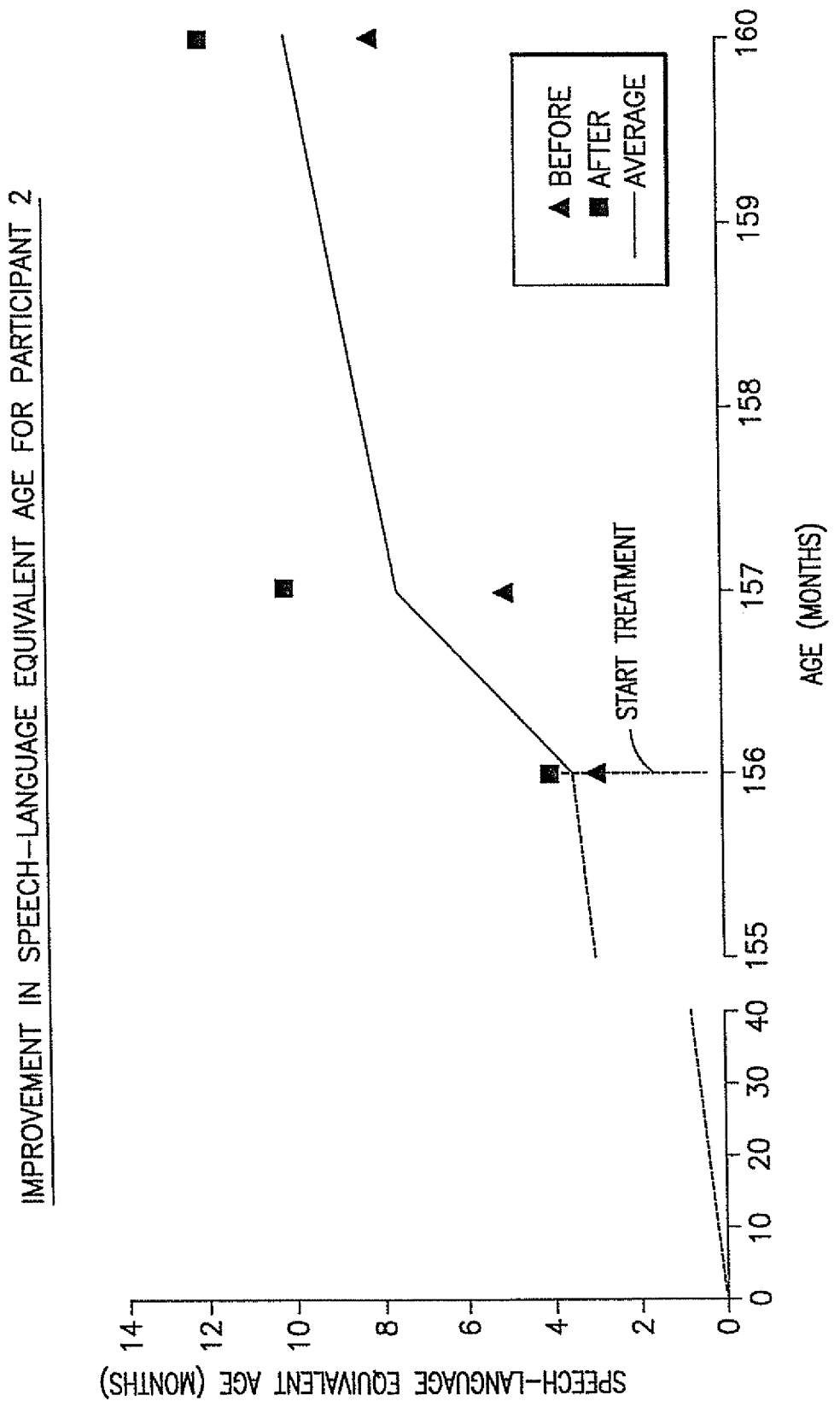

TREATMENT OF CEREBRAL PALSY IMPAIRED SPEECH IN CHILDREN

PRIOR RELATED APPLICATIONS

This application is a divisional application of U.S. patent application Ser. No. 14/059,541, filed Oct. 22, 2013, which is a continuation-in-part of U.S. patent application Ser. No. 14/112,065, filed Dec. 24, 3013 and a continuation-in-part of PCT/US2012/038312, filed May 17, 2012, which claims priority to provisional application No. 61/487,847, filed May 19, 2011, and claims priority to continuation-in-part U.S. patent application Ser. No. 14/182,332, filed Feb. 18, 2014 and which applications are incorporated herein in their entireties by reference thereto.

BACKGROUND OF THE INVENTION

1. Field of the Invention

This invention relates to cerebral palsy impaired speech. This invention also relates to evaluating a subject for and the treatment of a speech impairment secondary to cerebral palsy. In one specific aspect, this invention relates to the treatment of cerebral palsy impaired speech in children and adolescents. This invention also relates to speech, language and communication disorders in children diagnosed with cerebral palsy.

2. Background and Discussion of the Art

Cerebral palsy (CP) is a non-progressive disease or disorder involving irreparably damaged or injured areas of the brain, including connections between the cortex and other parts of the brain (the central nervous system) and the muscles (in the peripheral nervous system).

The National Institute of Neurological Disorders and Stroke (NINDS) of the National Institutes of Health (NIH) defines cerebral palsy as any of a number of neurological disorders that appear in infancy or early childhood and permanently affect body movement and muscle coordination but do not worsen over time, and then makes clear that cerebral palsy cannot be cured, but treatment will often improve a child's capabilities and that such treatment may include physical and occupational therapy, speech therapy, drugs to control seizures, relax muscle spasms, and alleviate pain; surgery to correct anatomical abnormalities or release tight muscles; braces and other orthotic devices; wheelchairs and rolling walkers; and communication aids such as computers with attached voice synthesizers.

There are several causes of cerebral palsy, including maternal trauma or infection resulting in periventricular leukomalacia, genetic mutations resulting in cerebral dysgenesis; fetal stroke resulting intracranial hemorrhage, and hypoxic ischemic encephalopathy. The several causes of cerebral palsy include complications before birth. Such complications may include genetic mutations resulting in cerebral dysgenesis, maternal or fetal infections resulting in encephalomalacia and intra-utero vascular thrombosis (intrauterine strokes). Complications during delivery may result in hypoxic-ischemic encephalopathy. After birth, CP can be the result of non-accidental trauma, encephalitis or meningitis due to any number of infectious or toxic agents.

There are generally three types of cerebral palsy, namely ataxic which includes lack of muscle coordination, spastic, which includes tighter muscles and exaggerated reflexes and movements, i.e. dyskinetic movements, which includes slow and uncontrollable withering. Spastic cerebral palsy is further defined as spastic diplegia and spastic quadriplegia.

Dysarthria is a neurogenic speech disorder that causes dysfunctional speech musculature, that is, tongue, lips, soft palate, facial muscles and larynx. There is low muscle tone or even paralysis of the speech muscles that coordinate with the speech functions. Children suffering from dysarthria are characterized by early sucking, chewing and swallowing problems. Many children "drool" for a long time and continue eating soft foods as they are easy to digest. These children also gag and choke frequently. Dysarthria can be classified as mild-to-moderate, wherein the patient slurs at least some words and, at best, can be understood with some difficulty; or severe, wherein the patent's speech is so slurred as to be unintelligible. Cerebral palsy is a cause of dysarthria. One speech impairment secondary to cerebral palsy is dysarthric speech. Non-bilabial speech is considered to be severe dysarthric speech. Dysarthria is one of the speech impairments treated by the present invention.

The National Institutes of Health (NIH) reports that conventional speech and language therapy for children with cerebral palsy might somewhat improve their communication skills. The NIH summarizes the status of speech muscular therapy attempts to treat cerebral palsy, impaired speech or attempts that can include ways of enhancing natural forms of communication, introducing aids such as symbol charts or devices with synthetic speech, and training communication partners. The NIH finds some weak evidence that speech and language therapy might help children with CP, but more research is needed.

Intensive speech and language therapy over the course of several weeks, such as disclosed in *Intensive Speech and Language Therapy for Older Children with Cerebral Palsy; a Systems Approach*, Pennington et al., Developmental Medicine & Child Neurology; 2010, 52: 337-344, reports at best a 14% to 16% improvement in the number of single or multiple word responses.

Various mechanical and electro-mechanical devices including electrodes are disclosed in the prior art for treating cerebral palsy impaired speech in children. Such devices are disclosed in U.S. Pat. No. 5,213,553, issued May 25, 1993 to Light; and US2006/0161218, published Jul. 20, 2006 to Danilov, Such treatments have had limited improvement in cerebral palsy impaired speech.

The art related to treating a speech impairment secondary to cerebral palsy in children desires a treatment that readily and substantially diminishes the impairment. The art also desires a treatment as aforesaid wherein the improvement in speech persists without the need for continuous treatment. The present invention accordingly provides a solution.

SUMMARY OF THE INVENTION

This invention in one principal aspect is the psychostimulant treatment of a speech and language impairment secondary to cerebral palsy. The invention in another aspect is the psychostimulant treatment of dysarthria in children and adolescents.

This invention in another principal aspect is the evaluation of a subject for the psychostimulant treatment of a speech impairment secondary to cerebral palsy. More specifically, the invention is a method for evaluating a subject for the psychostimulant treatment of a speech impairment secondary to cerebral palsy by diagnosing the subject as having cerebral palsy, determining that the subject has a resultant speech impairment, and then determining that the subject has threshold cognitive capability, and wherein when the subject has cerebral palsy impaired speech and the threshold cognitive capability, the subject is a candidate for psychostimulant treatment to diminish the impaired speech. A cognitive capability, as determined by art cognizable non-verbal techniques, of at least about two years is considered a threshold cognitive capability. The criteria used to select participants for this invention includes a medical and developmental history and pediatric neurological examination, in addition to a diagnosis of cerebral palsy. The classification of the patient's specific cerebral palsy (e.g. spastic, ataxic, and or dyskinetic) was not particularly a parameter that was considered. The candidates for treatment were required to posses the cognitive abilities equivalent to about a two year old child. These skills included but were not limited to following two-step unrelated commands, using a fisted grasp on a pencil to produce vertical strokes on paper, use of basic two-word combinations and in the non-verbal child, the ability to sequence his limited vocalizations and body movements to a rhythm when modeled (e.g., beat gestures develop at 24-27 months).

This invention in a more specific aspect is a method for treating cerebral palsy impaired speech in children and adolescents by the administration of a therapeutically effective dose of a psychostimulant to effect a decrease in the difference between chronological age and speech-language equivalent age. In one specific aspect, the present treatment results in the correct pronunciation of the bilabial consonants, syllables and polysyllables, in a child or adolescent with non-bilabial speech.

The invention is, in one further aspect, a dosage regimen for the treatment of cerebral palsy severe dysarthria by administration of a modest dose of a psychostimulant, with immediate resultant diminishment of the impaired speech. Where the impaired speech is non-bilabial speech and the inability to correctly pronounce the bilabial consonants is severe so as to be unintelligible, the bilabial consonants are correctly pronounced immediately after a single administration of the psychostimulant, and the dosage regimen administered over a period of time eventually results in the correct pronunciation of polysyllables.

The invention, as afore-discussed, with periodic administrations of the psychostimulant over the course of several weeks, provides persistent increasing diminishment of the impaired speech, and the percentage increase in the percentage of correctly pronounced syllables and words is from at least about 20 percent and upwards to several hundred percent.

In one further aspect, the present invention is a method for determining a subject suitable for psychostimulant treatment of a speech impairment secondary to cerebral palsy, as afore-discussed, which method further includes determining (i) in the subject that the subject is following two-step related commands; and (ii) in a verbal subject, determining that the subject is using basic two-word combinations; and (iii) in a non-verbal subject determining that the subject is: (A) sequencing limited vocalizations; and (B) moving the body to a rhythm when modeled.

Without wishing to be bound by any theory or mechanism, it is believed that the administration of a psychostimulant in a child or adolescent with a speech impairment secondary to cerebral palsy creates alternate neural pathways between the auditory cortex and the frontal lobe, which neural pathways circumvent the inoperable or damaged portions of the brain.

BRIEF DESCRIPTION OF THE DRAWINGS

FIG. 4 shows the improvement in speech-language equivalence age for Participant 2;

DESCRIPTION OF THE INVENTION

Definitions

Figure 1:
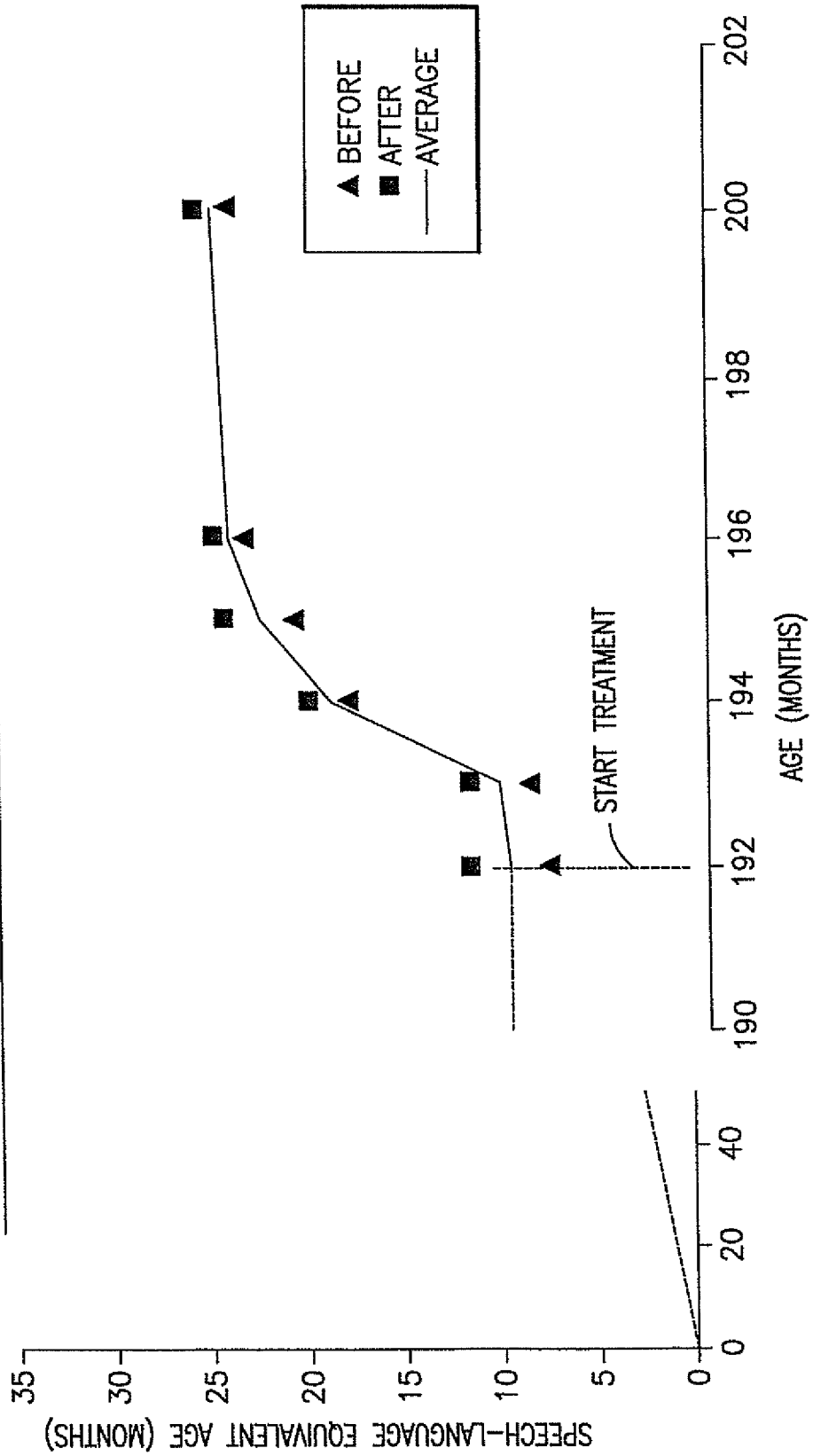
FIG. 1 shows the speech-language functional age of Participant 1 before and with treatment pursuant to the present invention.

The term "subject" as used hereinbefore and hereinafter means a human or other mammal, and includes a patient or participant in a study or clinical trial.

The term "therapeutically effective dose" or "therapeutically effective dosage" as used hereinbefore and hereinafter means an amount of the administered substance that is sufficient to provide a diminishment of the speech impairment.

The term "psychostimulant" as used hereinbefore and hereinafter is broadly defined as a drug having antidepressant or mood-elevating properties, and as further discussed hereinafter.

The term "speech impairment secondary to cerebral palsy" is an art cognizable term and further contemplates language impairments.

The term "bilabial consonants" as used hereinbefore and hereinafter means, in the English language, the consonants m/p/b/w. And "non-bilabial speech" means the inability to correctly pronounce one of more of the bilabial consonants.

The term "speech-language age equivalence" or "speech-language equivalent age" is the functional speech age of the participant, as determined by a speech therapist by methodologies well-known in the speech therapy art, and as further discussed in co-pending application PCT/US2012/038312, filed May 17, 2012 and incorporated herein in its entirety by reference thereto.

EXAMPLES

In each of the following examples, the correctly pronounced intelligible syllables or words, if any, prior to administration of the psychostimulant is measured against the correctly pronounced intelligible syllables or words after administration of the psychostimulant. Specifically, correctly produced sounds, syllables or words and the use of language prior to the administration of the psychostimulant is used as a baseline to measure against a participant's production after the administration of psychostimulant.

Participant 1

Participant 1 is a 16 year old boy diagnosed with cerebral palsy resulting from hypoxic-ischemic encephalopathy (i.e., lack of oxygen to the brain during birth). This in turn resulted in extremely limited production of sounds that are not intelligible and cannot be combined to approximate words, and is a bilabial speech impairment. The speech-language age equivalency was measured before the administration and approximately 30 minutes after the administration of the psychostimulant methylphenidate in periodic treatment sessions. The number of correct or intelligible response was measured before and after each treatment session. Before the first treatment session (Session 1), Participant 1 could not imitate sounds, was unable to produce modeled sounds in isolation and the beginning, middle or end of words. Participant 1 was unable to pronounce his own name. Participant 1 had no cognizable sound production. Participant 1, before treatment, had a speech-language age equivalence of a 3 month old child. Participant 1 has a cognitive functional age of a 3½ year old child, as determined by non-verbal techniques well known in the field. Participant 1 was administered methylphenidate 5.0 mg/day approximately three times a week.

Participant 1, prior to the first administration of methylphenidate in Session 1, correctly imitated 5 words in 52 attempts, and after the first administration correctly imitated 18 words in 56 attempts. This represents an about 250% increase in the number of correctly pronounced or intelligible syllables or words. Participant 1, as reported in Table I below, correctly imitated 9.61% of the speech before the initial administration of 0.5 mg methylphenidate, and within about 30 minutes after the initial administration correctly imitated 32.14% of the speech, or an about 300% improvement in the percentage correct speech imitations.

Figure 2:
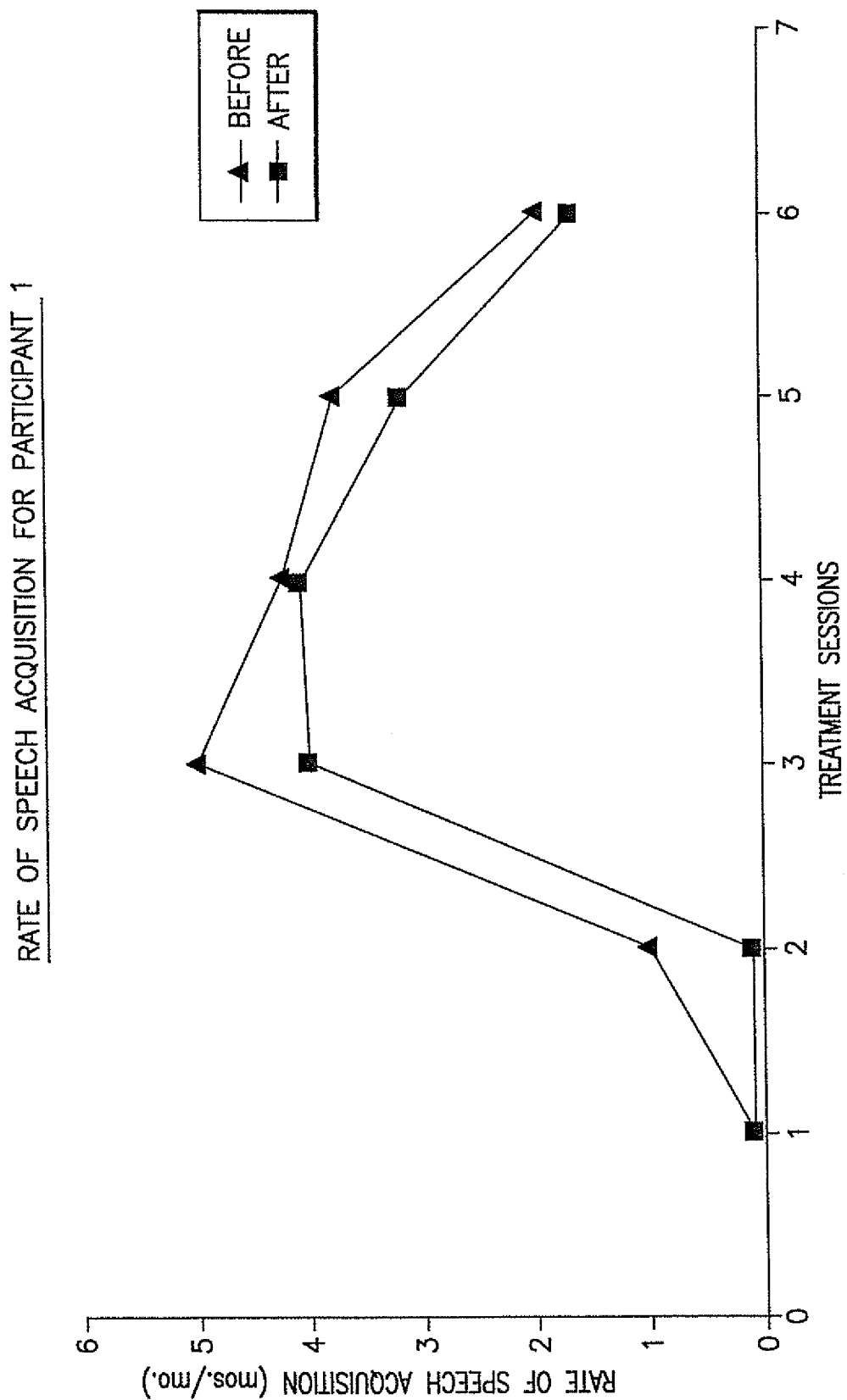
FIG. 2 shows the rate of speech acquisition of Participant 1 over the course of several treatment sessions.

FIG. 1 shows the speech-language age equivalence vs. the actual age for Participant 1 over the course of treatment. FIG. 2 shows the rate (months/month) of speech acquisition for Participant 1. After six months, Participant 1 had established a speed-language equivalent age of about 25 months. Participant 1 had a phonetic improvement that persisted after the methylphenidate was no longer efficaciously present in the subject and prior to a subsequent administration of methylphenidate.

Figure 3:
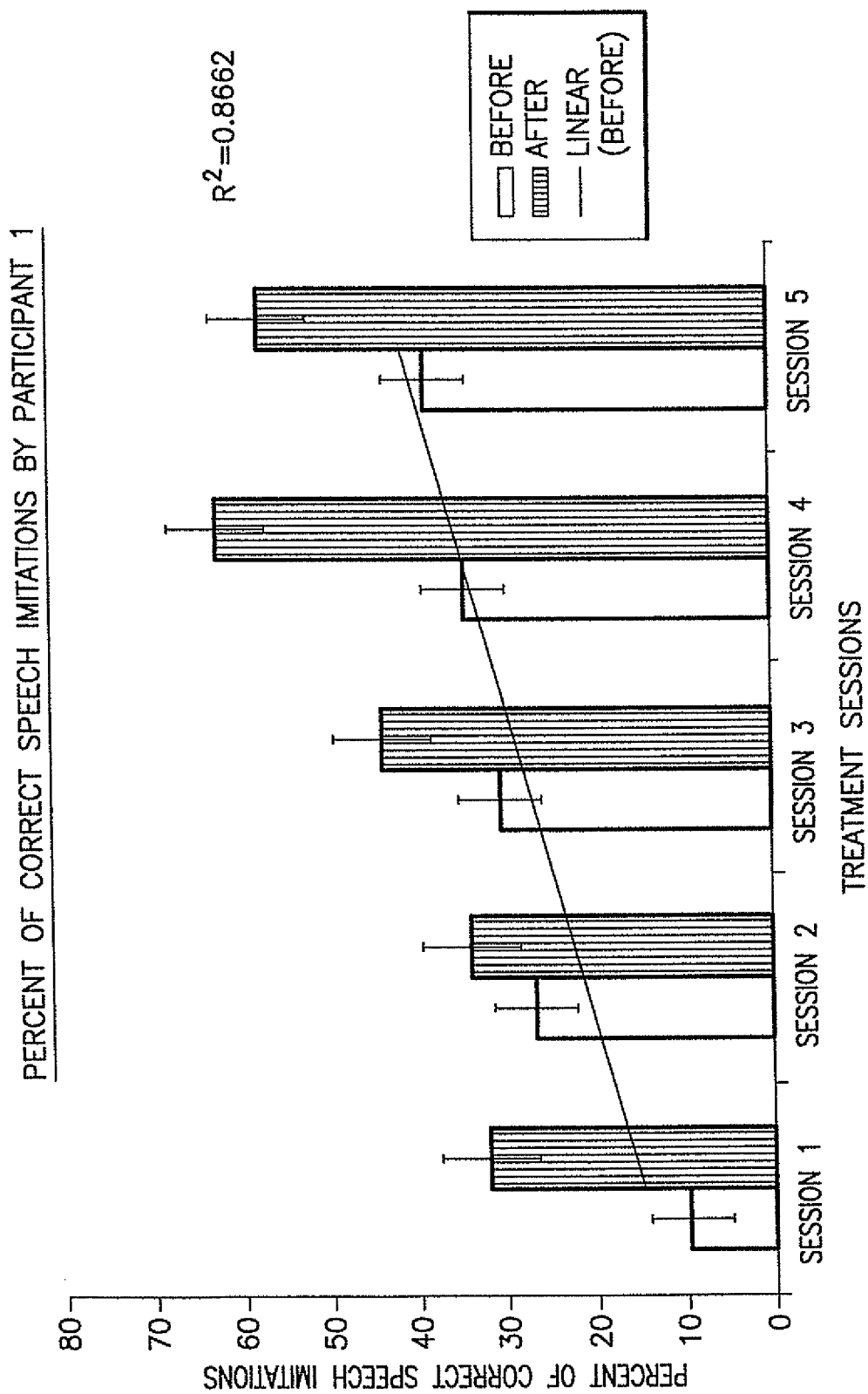
FIG. 3 shows the percent of correct speech imitations for Participant 1 over the course of the treatment sessions for Participant 1.

FIG. 3 shows bar grafts representing the percent of correct word limitations over the course of five treatment sessions. The (Before) bar graphs and averaging slope line for Sessions 1-5 demonstrate a continued persistent improvement.

Figure 3A:
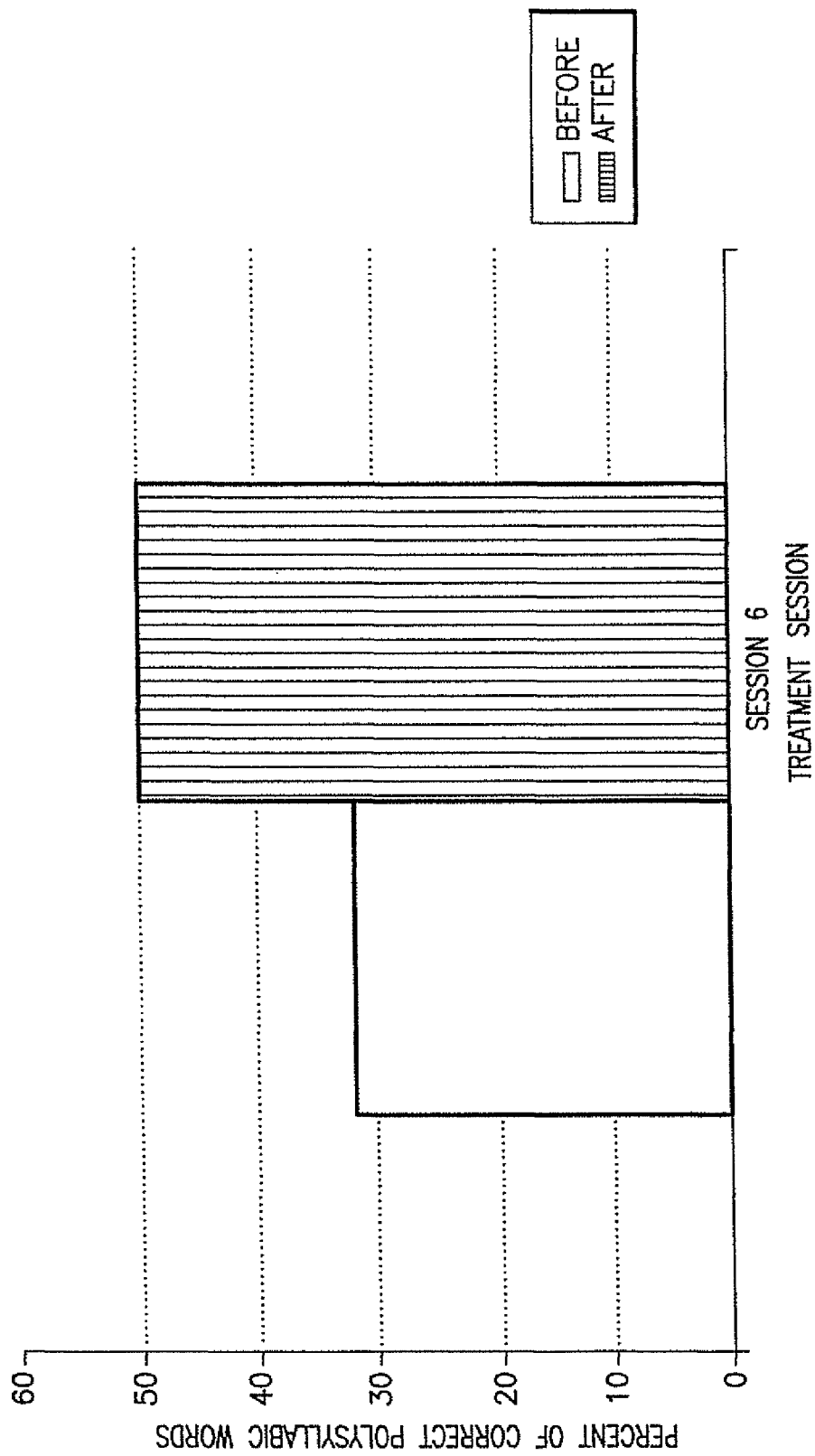
FIG. 3A shows the percent of correct pronunciation of polysyllabic words by Participant 1 in session 6.

FIG. 3A shows the percent of correct responses before and after treatment for Participant 1 in Session 6. Session 6 is particularly significant in that Participant 1 was first challenged with polysyllabic words. Participant 1 was provided with the art cognizable PROMPT assistance techniques administered by a speech therapist before and after administration of the psychostimulant methylphenidate in treatment Sessions 1-5. Participant I however was afforded no PROMPT assistance before or after administration of the psychostimulant dextroamphetamine in the polysyllabic word challenge of Session 6. In Session 6, Participant 1 correctly imitated 31.87% of the polysyllabic words prior to administration of the dextroamphetamine and 40% of the polysyllabic words after administration of the dextroamphetamine, or an about 18% improvement (FIG. 3A).

The following Table I shows percent of correct word responses for Participant 1 and the percent improvement for each session.

TABLE 1

Percent of Correct Speech Imitations for Participant 1

| TREATMENT SESSIONS | BEFORE | AFTER | DIFFERENTIAL |
|---|---|---|---|
| Session 1 | 9.61% | 32.14% | 22.53 |
| Session 2 | 26.83% | 33.96% | 7.13 |
| Session 3 | 30.68% | 43.81% | 13.13 |
| Session 4 | 34.62% | 61.9% | 27.28 |
| Session 5 | 38.98% | 57.14% | 18.16 |
| Session 6 | 31.87% | 40.00% | 18.13 |

Participant 2

Participant 2 is a 13 year old girl. Participant 2 was diagnosed with hypoxic ischemic encephalopathy cerebral palsy resulting in unintelligible speech consisting of merely inaudible vowel sounds. An MRI for Participant 2 showed symmetric areas of gliosis and encephalomalacia involving bilateral temporal, frontal and parietal lobes consistent with chronic infarcts in the vascular territories of the middle cerebral arteries. There were smaller focal areas of encephalomalacia and gliosis involving the occipital lobes, right greater than the left. It was determined that Participant 2 had a cognitive capability age of at least about a 2 year old. Prior to treatment, Participant 2 had a speech-language age equivalence of a 3 month old. Participant 2 was treated with 5.0 mg of immediate release methylphenidate in three treatment sessions over a period of approximately three months. The speech-language age equivalence was measured before and approximately 30 minutes after each administration in the treatment session.

FIG. 4 shows the improvement in speech-language age equivalence for Participant 2 from the date of first treatment wherein prior to the first treatment Participant 2 had a speech-language age equivalence of a three month old, and after three treatment sessions over a three month period, Participant 2 had a speech-language equivalence of a 14 month old.

Figure 5:
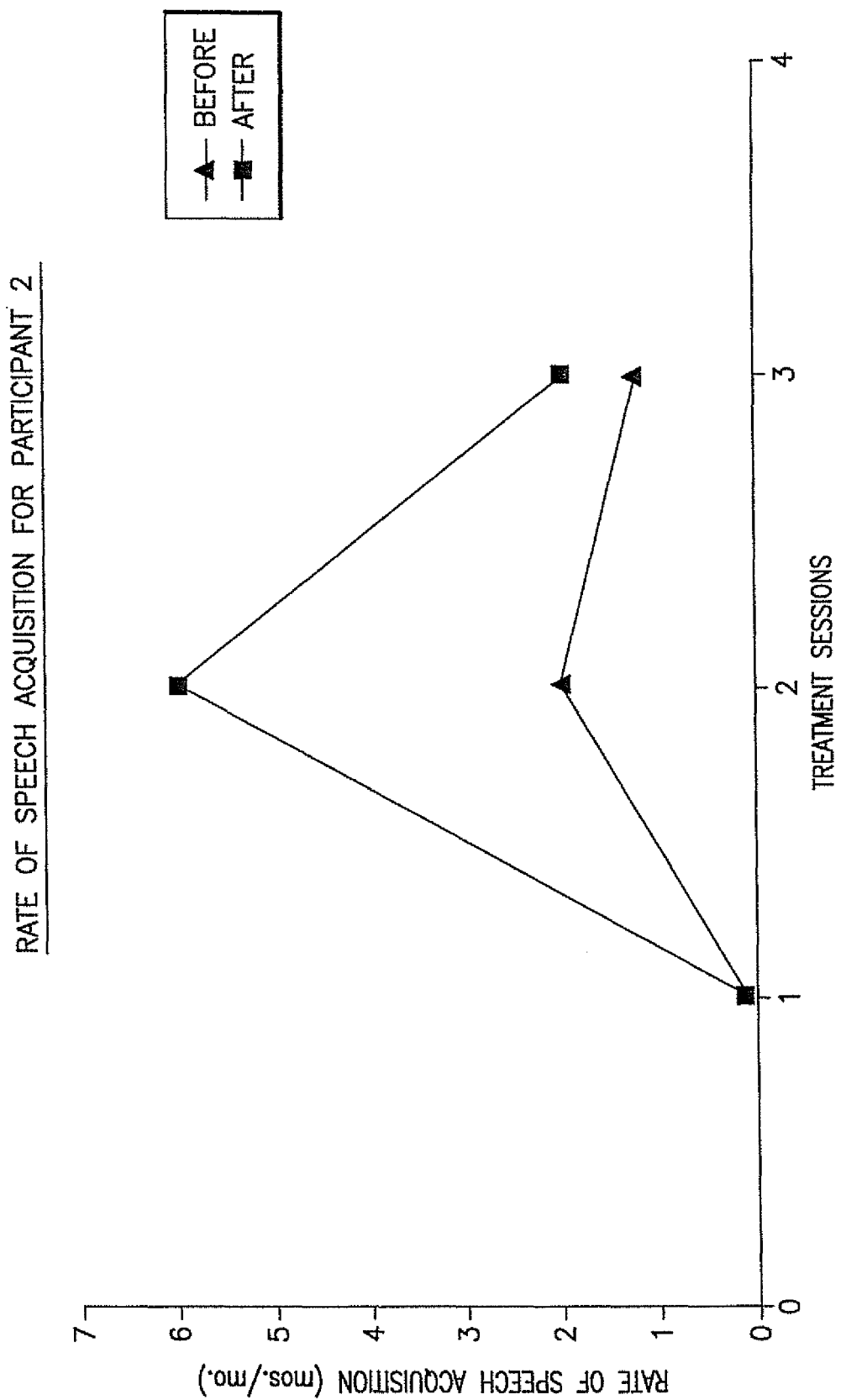
FIG. 5 shows the rate of speech or sound acquisition for Participant 2.

FIG. 5 shows the rate (months/month) of sound acquisition for Participant 2 for the treatment sessions. Prior to the psychostimulant treatment, despite having received conventional speech and language therapy, Participant 2 had a speech-language age equivalence of a three month old. After the treatment sessions, Participant 2 had a rate of sound acquisition of greater than about 35 months/year, whereas prior to the first treatment, the rate of sound acquisition was 3 months/13 years or 0.23 months/year.

Figure 6:
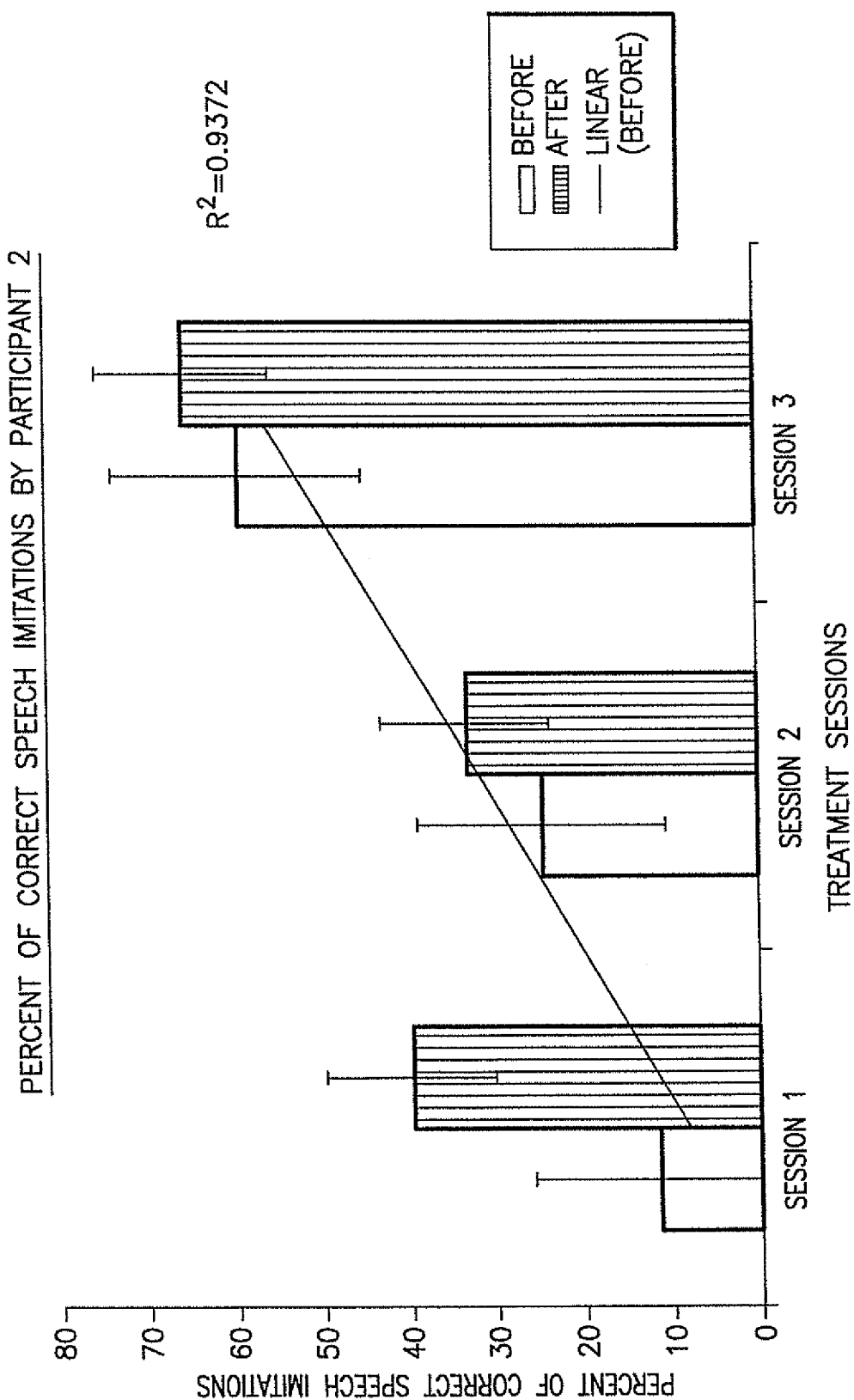
FIG. 6 shows the percent of correct speech imitations by Participant 2.

FIG. 6 shows the percent of correct imitations of speech for three successive treatment sessions. The FIG. 6 linear slope (Before) demonstrates the persistent increasing percentage of correct speech imitations, even before subsequent administrations of the methylphenidate in the treatment session. The vertical lines in all bar graphs for all Participants represent the range of measurements before and after administration of the psychostimulant.

Referring specifically to FIG. 4, there is shown the percentage correctly pronounced syllables or words as about 10% prior to a first administration of the psychostimulant methylphenidate and more than 30% after a single administration of the psychostimulant methylphenidate, or an increase of about 200% in the percentage of correctly pronounced intelligible syllables or words, in the first administration. In Session 2, Participant 2 initially could not pronounce any of the syllables or words prior to administration, but the percentage of correctly pronounced intelligible syllables or words after Session 2 administration was more than 40%. The percentage of correctly pronounced and intelligible syllables or words, both before and after administration of the psychostimulant methylphenidate generally progressively increased from week 1 through week 3. This demonstrates persistent continued improvement, in contradistinction to transient improvement, in the diminishment of the speech impairment. There was persistent improvement, even when the polychostimulant was no longer efficaciously present in the body.

Table II shows the percent of correct speech imitations for Participant 2.

TABLE II

Percent of Correct Speech Imitations for Participant 2

| SESSIONS | BEFORE | AFTER | DIFFERENTIAL |
|---|---|---|---|
| Session 1 | 10% | 34.09% | 24.09 |
| Session 2 | 21.21% | 28.57% | 7.36 |
| Session 3 | 50.63% | 55.77% | 5.14 |

Participant 3 is an 8 year old girl with a Spanish speaking environment in early childhood. Participant 3 was diagnosed with cerebral palsy periventricular leukomalacia resulting from an in utero stroke. Participant 3, prior to treatment pursuant to the present invention, had the capacity to vocalize one word or at best a two word phrase when provided with a visual or pictorial prompt, and had a speech-language equivalent age of a two year old. Participant 3 was administered a dose of methylphenidate 5.0 mg/twice per day of methylphenidate, once after breakfast and after school. After six months, Participant 3 could speak four and five word phrases when provided with a visual or pictorial prompt.

Figure 7:
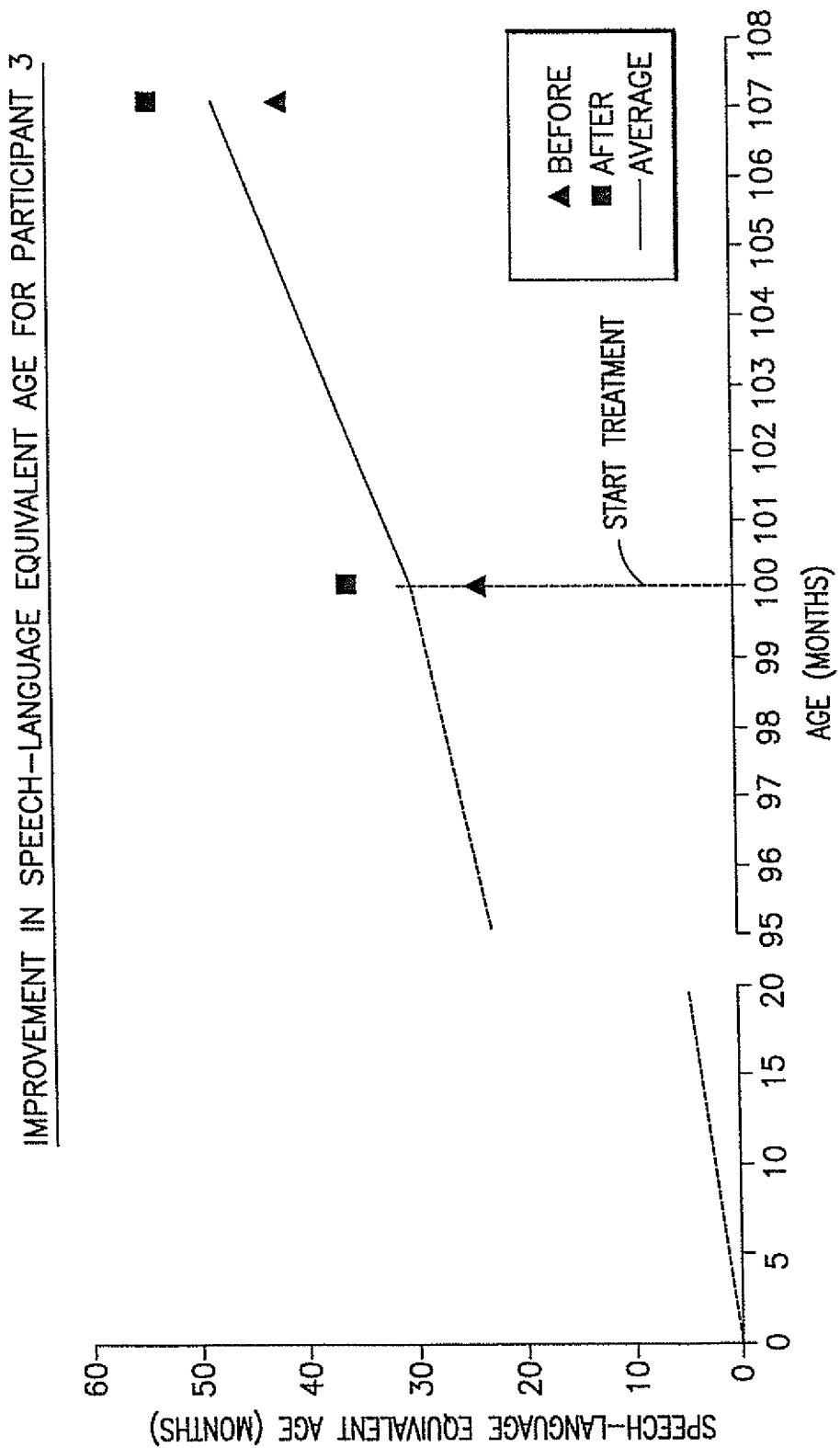
FIG. 7 shows the improvement in speech-language age equivalence for Participant 3.
Figure 8:
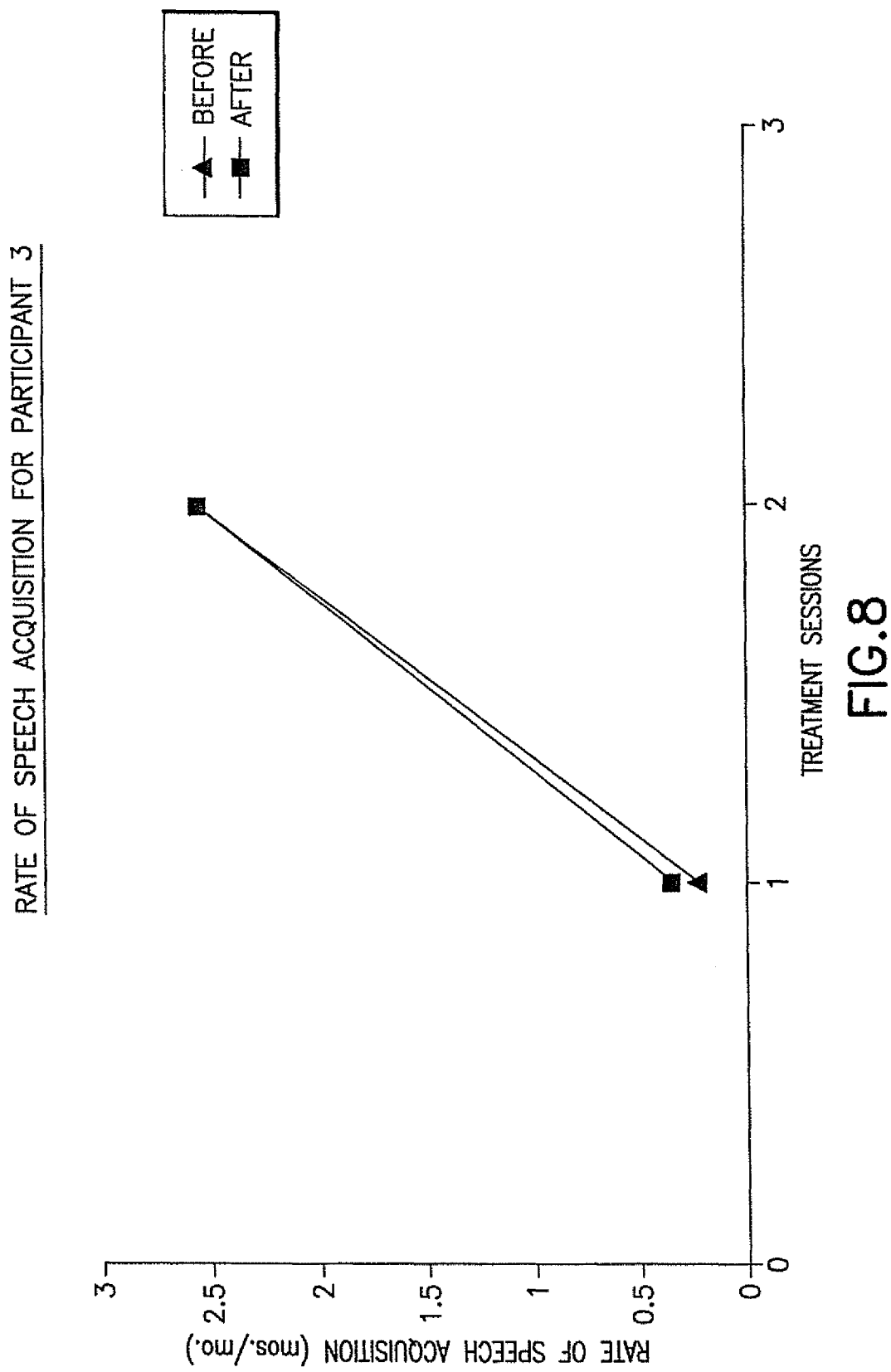
FIG. 8 shows the rate of speech acquisition for Participant 3.

FIG. 7 shows the improvement in speech-language equivalence for Participant 3 over the course of two treatment sessions. FIG. 8 shows the corresponding rate of speech acquisition for Participant 3. Participant 3 had acquired 2 years (24 months) of speech in the first 8 years (96 months), or a pre-treatment rate of speech acquisition of 0.4 mo./mo., and after a six month treatment period, had a speech acquisition rate of 3 years (36 mo.)/0.5 year (6 mo.) or 6.0 mo./mo. This represents more than about a 1,000% increase in the rate of speech acquisition.

Figure 9:
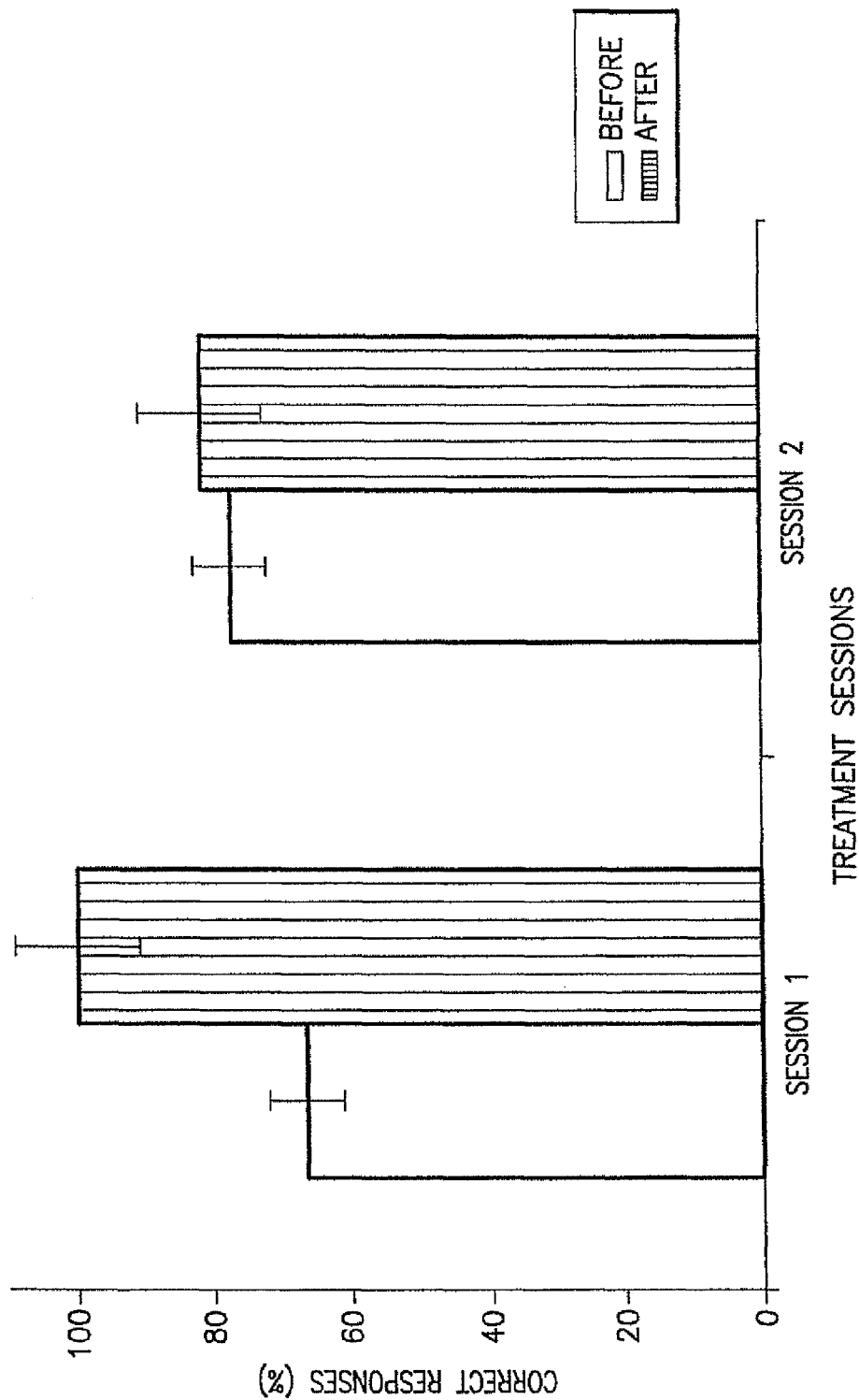
FIG. 9 shows the percent correct responses for Participant 3.

FIG. 9 shows the percent correct multi-word responses for Participant 3 after two treatment sessions. It is important to note that Participant 2 was challenged with more difficult phrases in the second session than in the first session and yet demonstrated significant improvement Participant 4 is an 8 year old girl with an Arabic speaking environment in early childhood. Participant 4 was diagnosed with vascular accident, Protein C deficiency cerebral palsy. The MRI for Participant 3 showed a large area of encephalomalacia in the right temporal and posterior frontal lobe with Wallerian degeneration and atrophy involving the right thalamus and right brain stem from the midbrain down to the medulla on the right side. Participant 4, prior to treatment, exhibited on average at best two word phrases, and a speech-language equivalence age of an 18 to 24 month. Participant 4 was administered 5.0 mg of methylphenidate in three treatment sessions spread over the course of 2 months. Participant 4's average response phrase length increased to five words, reflecting a speech-language age equivalence of a 6 year old (72 mos.).

Figure 10:
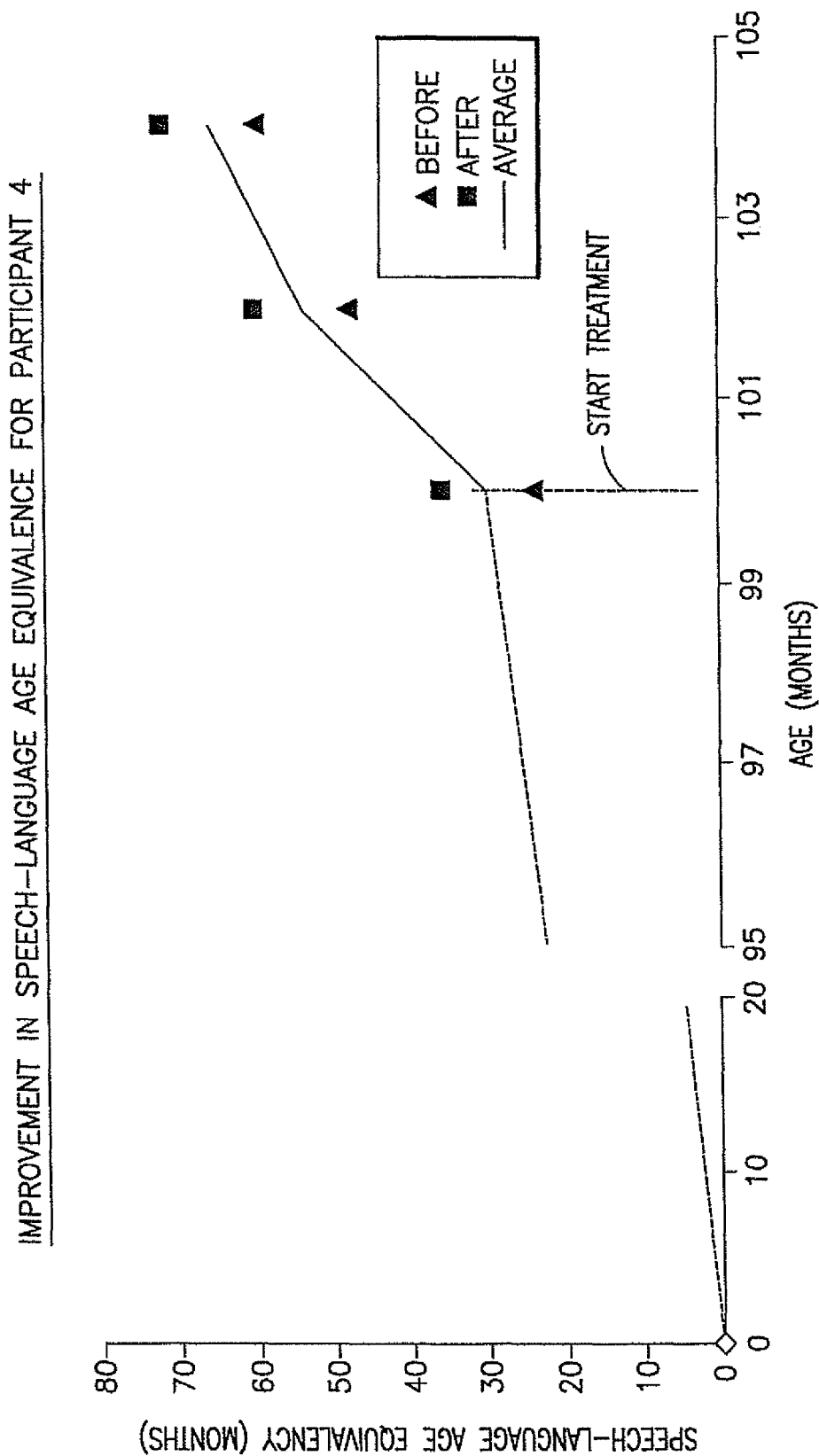
FIG. 10 shows the improvement in speech-language age for Participant 4.
Figure 11:
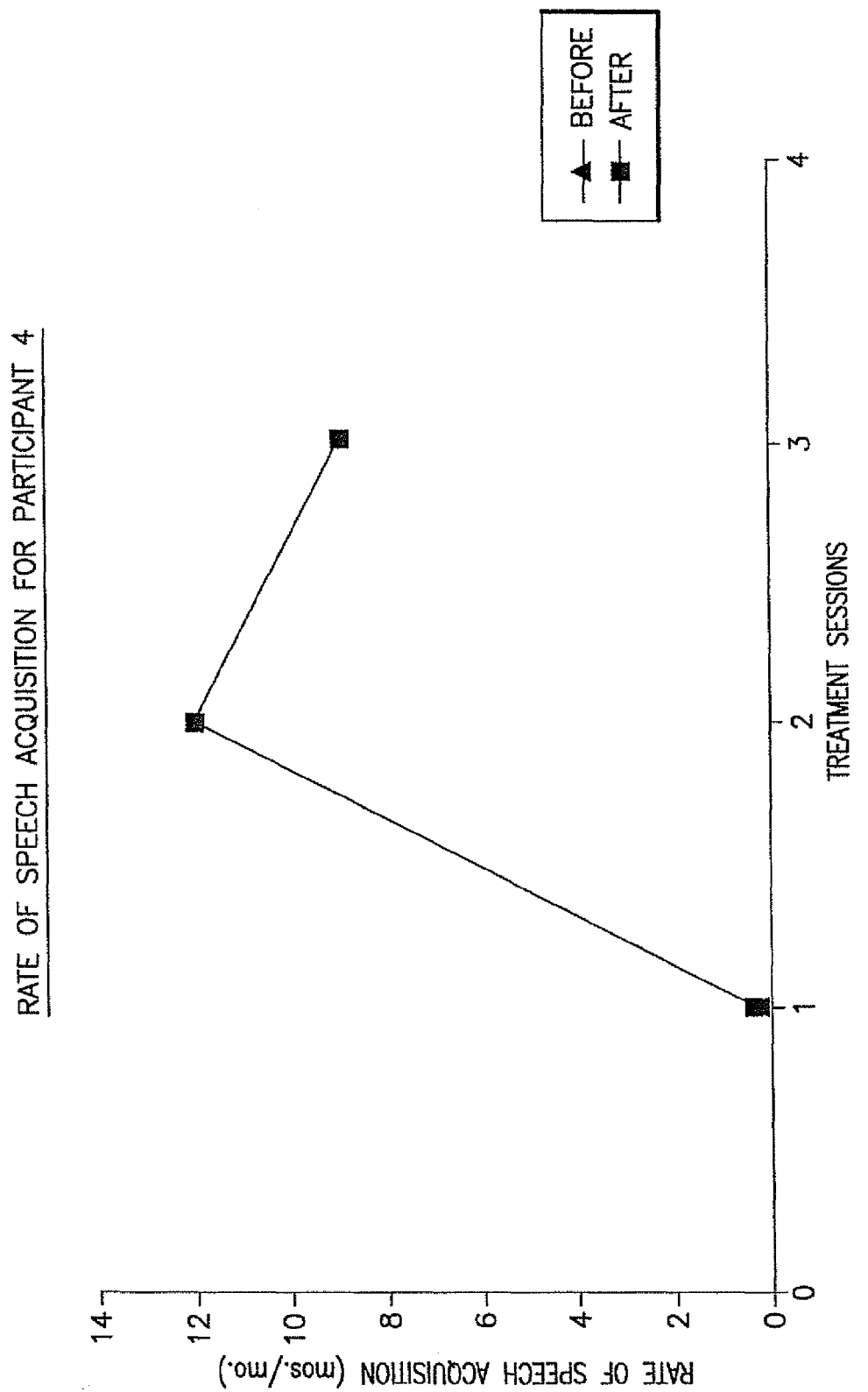
FIG. 11 shows the rate of speech acquisition for Participant 4.

FIG. 10 shows the improvement in speech-language equivalent age for Participant 4. FIG. 11 shows the rate of speech acquisition for Participant 4. Participant 4 had acquired, at best, 24 months of speech in her first 8 years (96 mos.) or a pre-treatment rate of speech acquisition of 0.25 mo./mo. After two months of treatment, Participant 4 acquired 4 years (48 mos.) or a rate of speech acquisition of 24 mo./mo.

Figure 12:
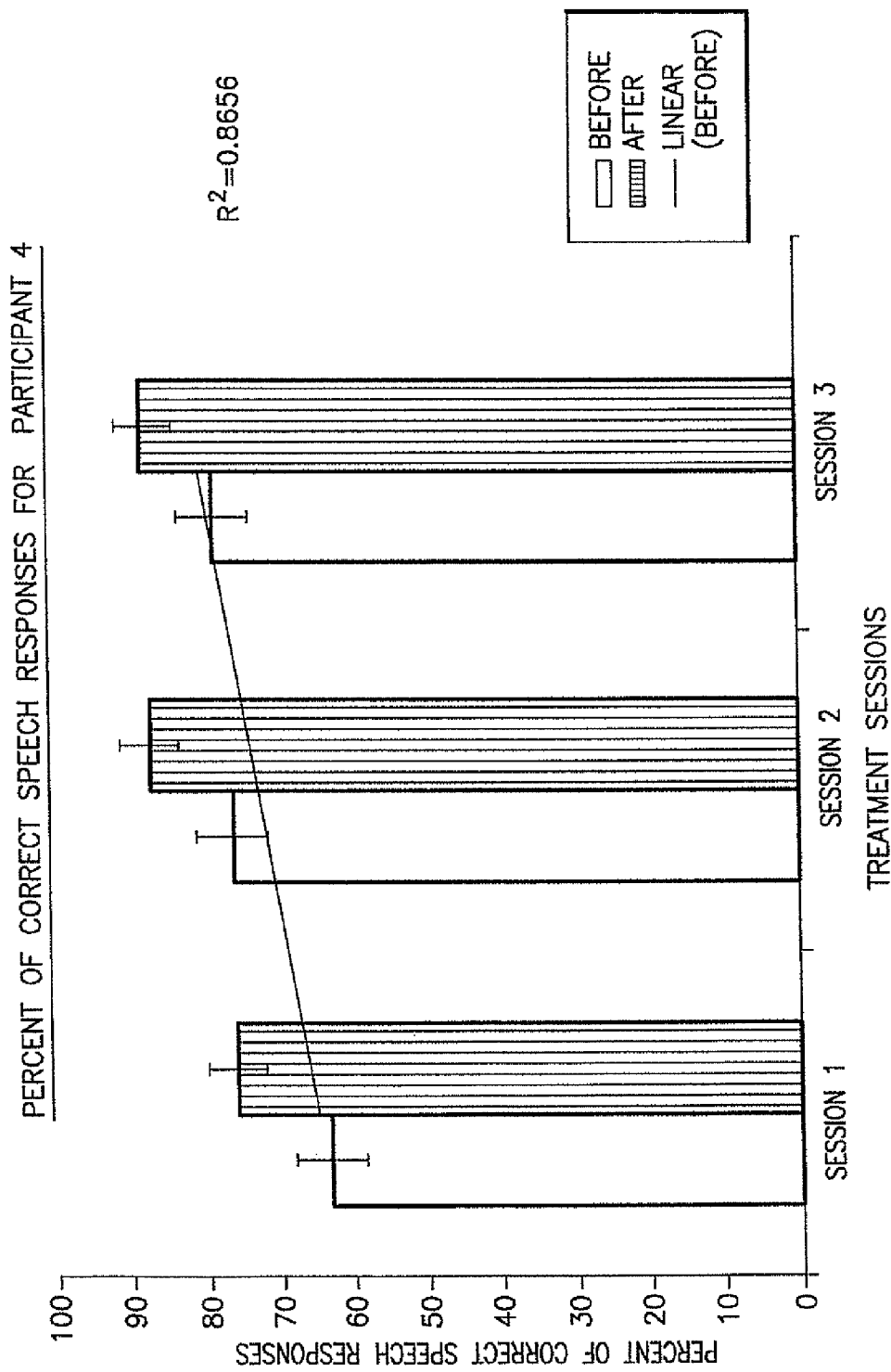
FIG. 12 shows the percent of correct speech responses for Participant 4.

FIG. 12 shows the percent of correct speech responses for Participant 4. As demonstrated by the linear (Before) averaging slope, there is a persistent increase in the percent of correct responses, even prior to the administration of the psychostimulant in a subsequent treatment session.

Participant 5 is a five year old girl diagnosed with genetic mutation cerebral palsy with a resultant speech impairment. Participant 5 had a cognitive ability greater that a two year old. Participant 5, prior to treatment, had unintelligible speech of about one or two word phrases, accompanied by multiple errors in articulation. Participant 5 was unable to imitate phonics that is appropriate for a three-year old. After four months of 5.0 mg immediate release methylphenidate in seven treatment sessions, Participant 5 was able to intelligently pronounce some consonants and polysyllabic words and phrases.

Figure 13:
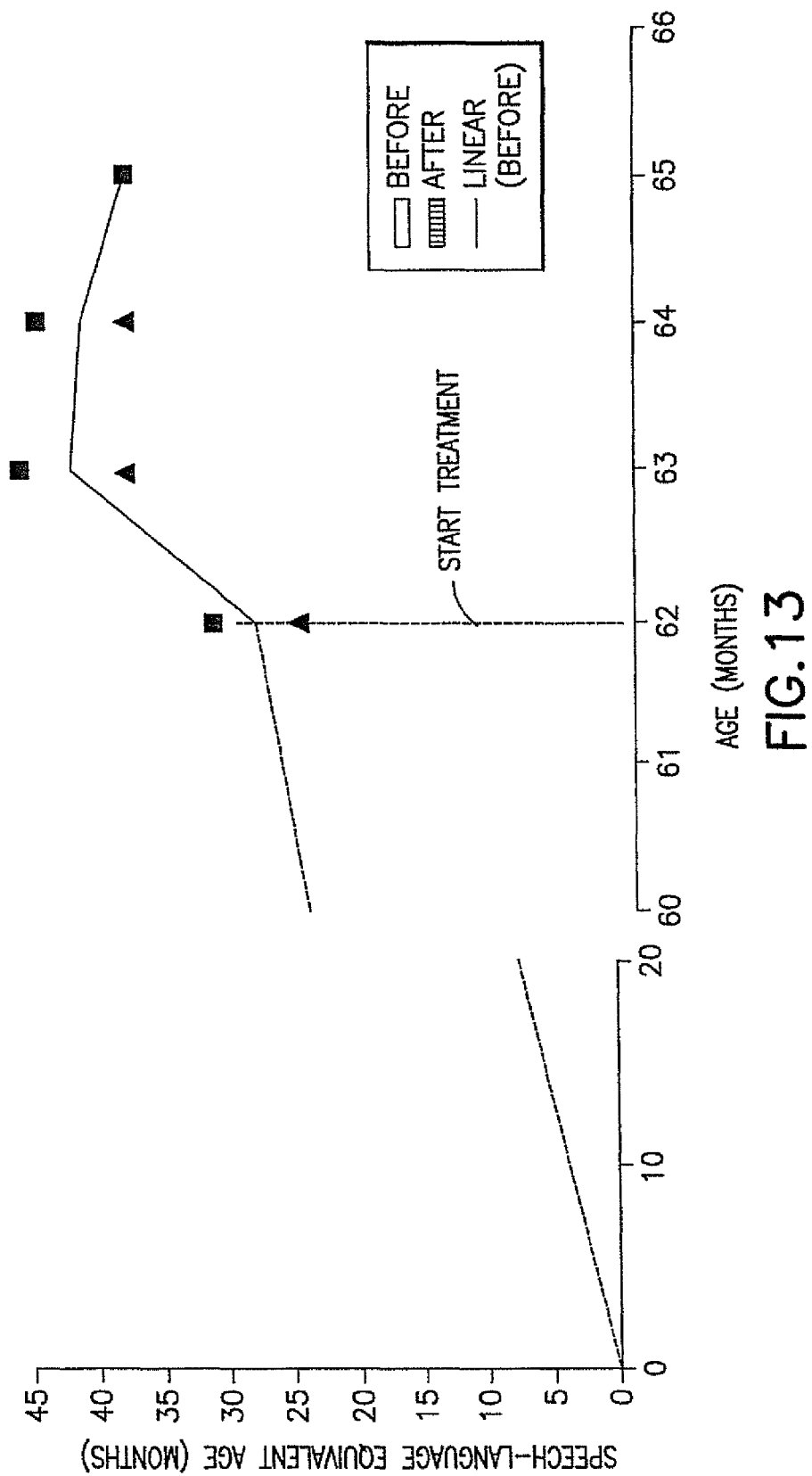
FIG. 13 shows the improvement in speech-language age equivalence for Participant 5.
Figure 14:
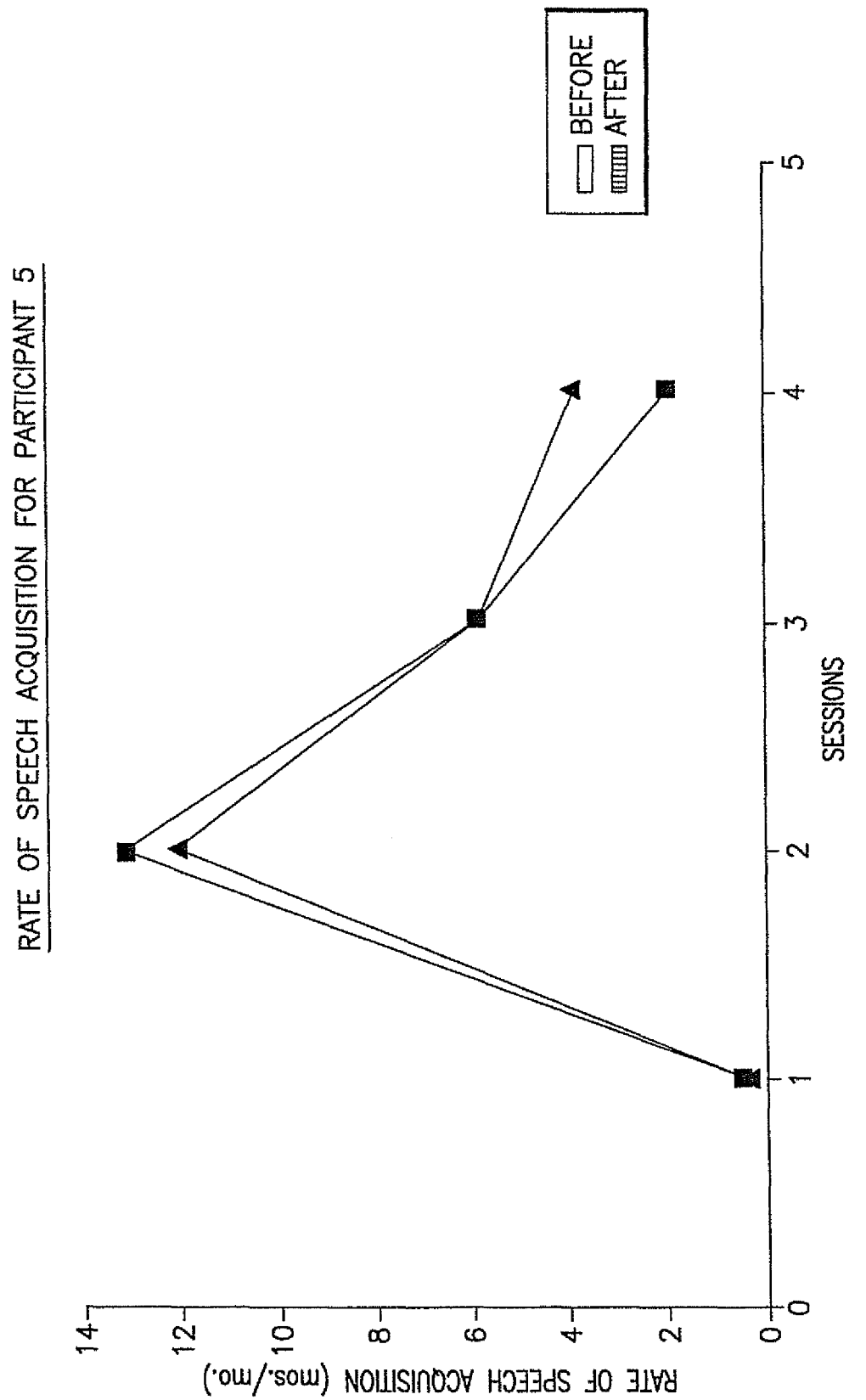
FIG. 14 shows the rate of speech acquisition for Participant 5.
Figure 15:
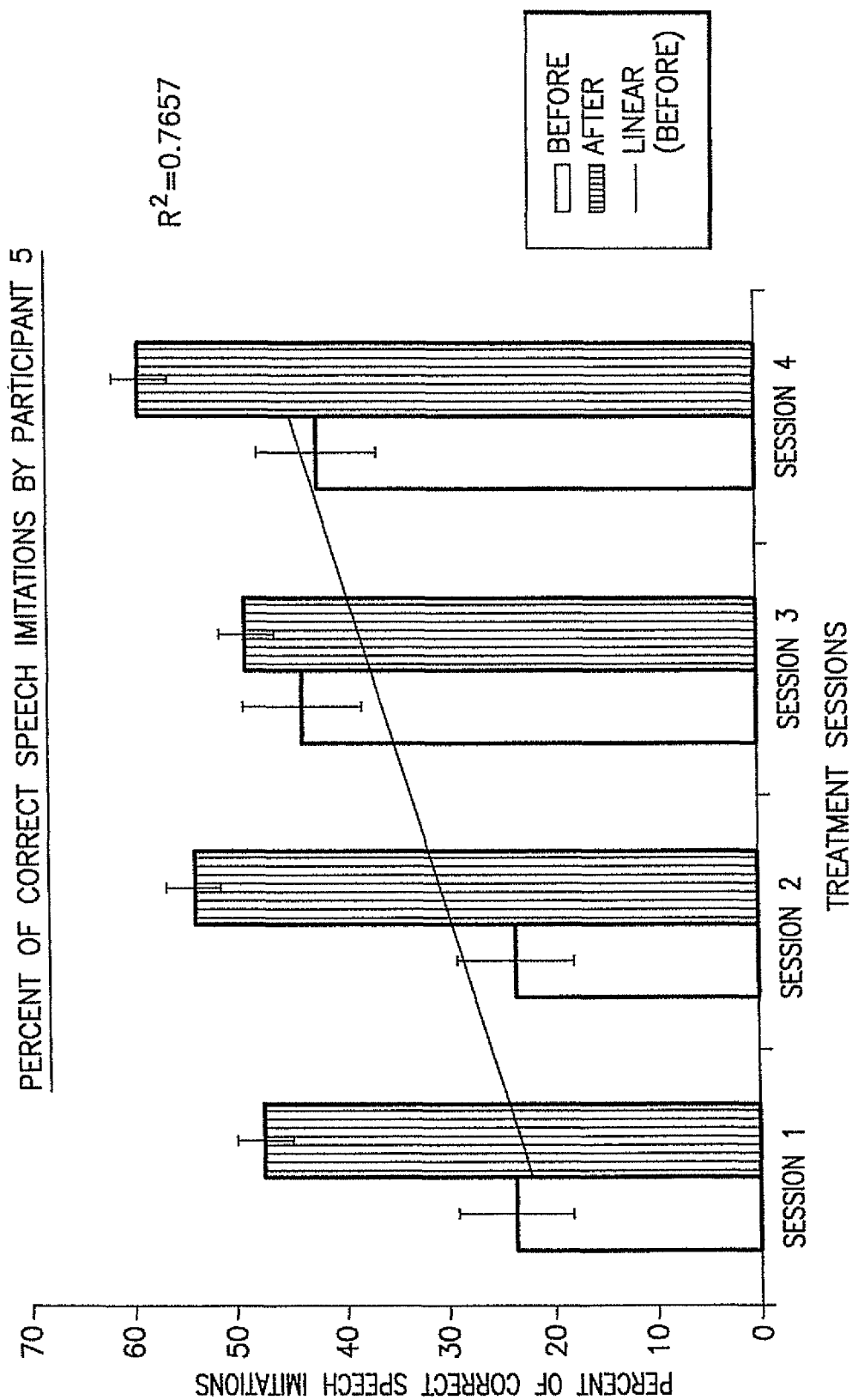
FIG. 15 shows the percent of correct speech imitations for Participant 5.

FIG. 13 shows the improvement in speech-language equivalence age for Participant 5 over the four months treatment sessions. FIG. 14 shows the percent correct speech imitation for Participant 5 over the course of the four treatment sessions. The linear (Before) averaging slope line demonstrates the persistent improvement in the percent of correct speech imitations over the course of treatment sessions, and continued improvement before psychostimulant administration in a subsequent treatment session.

Table III shows the percent correct speech imitations for Participant 5 before and after administration of the methylphenidate over the course of the four treatment sessions.

TABLE III

Percent of Correct Speech Imitations for Participant 5

| TREATMENT SESSIONS | BEFORE | AFTER | DIFFERENTIAL |
|---|---|---|---|
| Session 1 | 23.68% | 47.62% | 23.94 |
| Session 2 | 23.53% | 54.05% | 30.53 |
| Session 3 | 43.75% | 48.98% | 5.23 |
| Session 4 | 42.34% | 59.18% | 16.81 |

Figure 17:
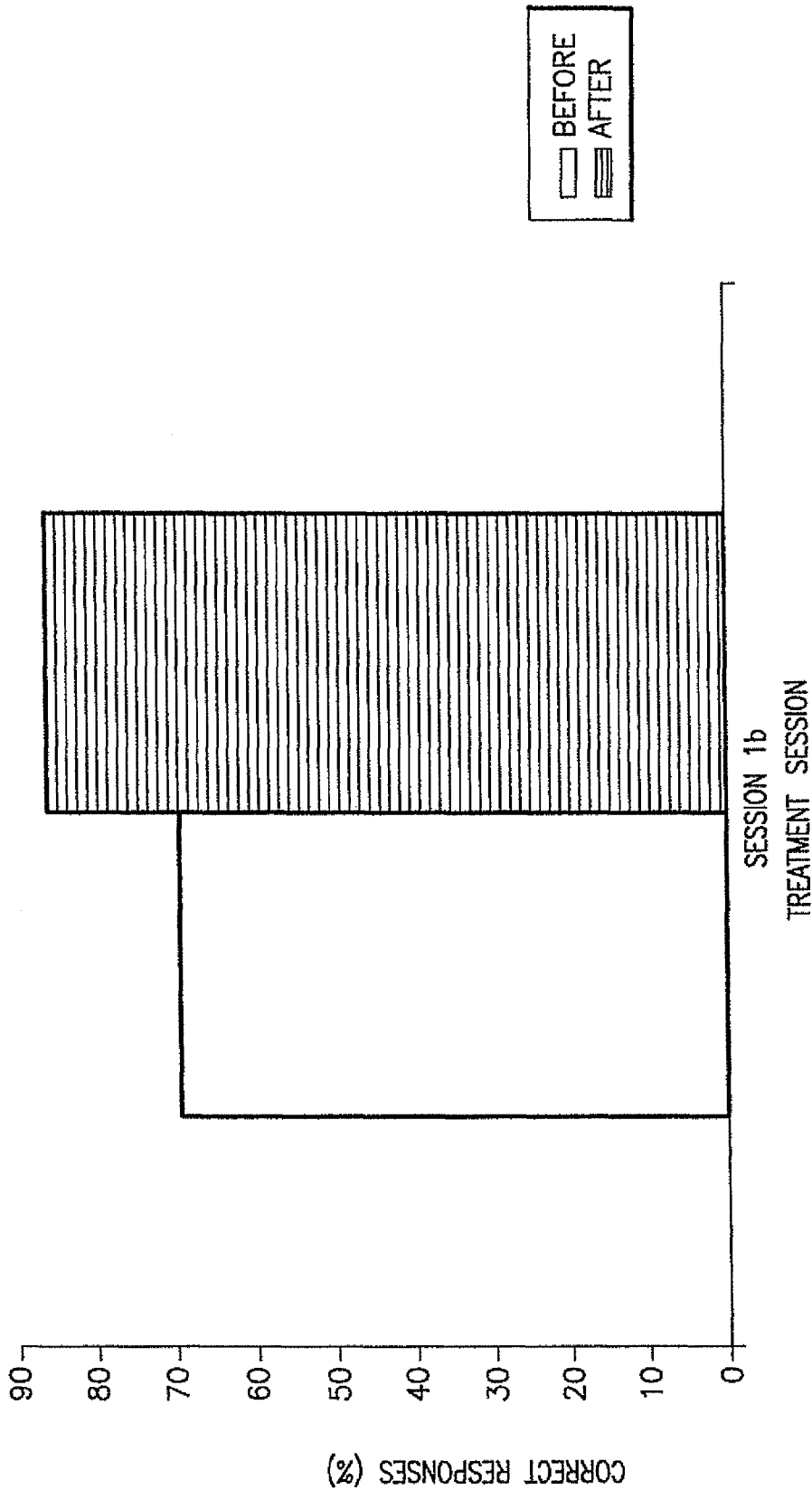
FIG. 17 shows the percent of correct speech responses for Participant 6 for Session 1b.

Participant 6 is a 16 year old adolescent boy. Participant 6 was diagnosed with Trisomy21 (Down Syndrome) cerebral palsy resulting in a speech impairment. On initial assessment, Participant 6 had the speech-language equivalent age of a 24 month old. In Session 1, a 5 mg. of immediate release methylphenidate was administered. There was an immediate follow-up post-preliminary Session 1b. A 5.0 mg dose of immediate release methylphenidate was administered in Session 1b. In Session 1b, Participant 6 had achieved a speech-language age equivalence of a 30 month old. FIG. 17 shows the percent of correct responses for Session 1b. A 10 mg dose of the amphetamine Dextroamphetamine was administered in Session 2. In Session 2, there was an increase in the speech-language equivalent to a 36 month old. A Between Sessions 1b and 2, there was a 10 day period in which Participant 6 received 0.5 mg methylphenidate/day. During this 10 day period Participant 6 experienced adverse side effects including loss of appetite and difficulty sleeping. Dextroamphetamine was accordingly administered in Session 2.

Figure 16:
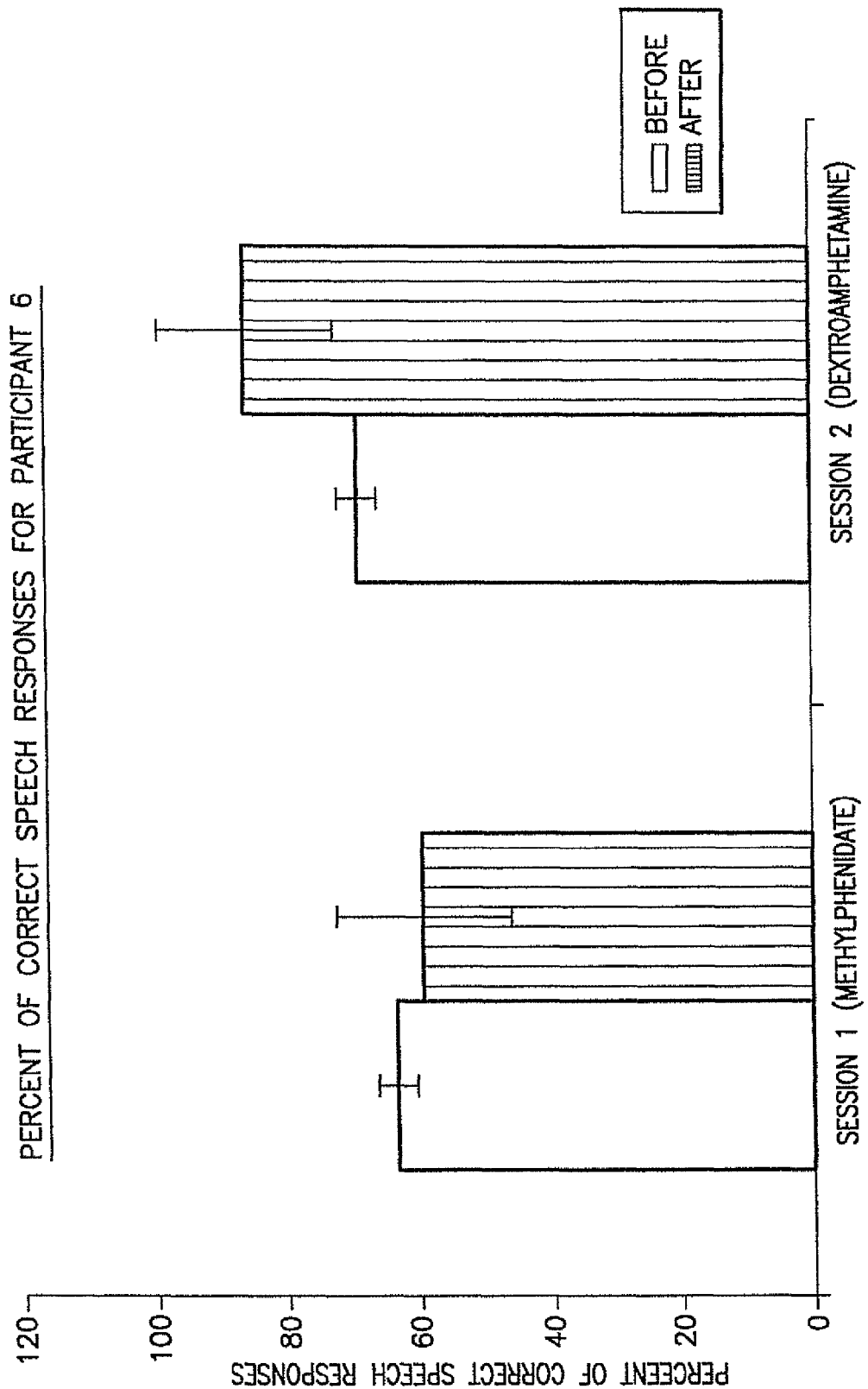
FIG. 16 shows the percent of correct speech responses for Participant 6 for Sessions 1 and 2.

FIG. 16 shows the percent of correct speech responses by Participant 6 in the two treatment sessions, and Table IV shows the numerical percent correct responses in Sessions 1 and 2. Table IV demonstrates that in Session 2, Participant 6 showed an about 17% increase in the percent correct responses after the single administration of 10 mg. of dextroamphetamine. Participant 6 had an apparent substantial increase in vocabulary access.

It is known in the art that certain non-verbal adolescents have self-promoting gestures to compensate for inadequate vocabulary. Such gestures were measured in Participant 6 before and after Sessions 1 and 2. There was a substantial decline in such gestures after Session 2. This decline experientially correlates with an increased access to and use of vocabulary.

TABLE IV

Percent of Correct Responses for Participant 6

| TREATMENT SESSIONS | BEFORE | AFTER | DIFFERENTIAL |
|---|---|---|---|
| Session 1 | 63.16% | 59.26% | −4.10 |
| Session 2 | 69.05% | 85.71% | 16.66 |

Figure 18:
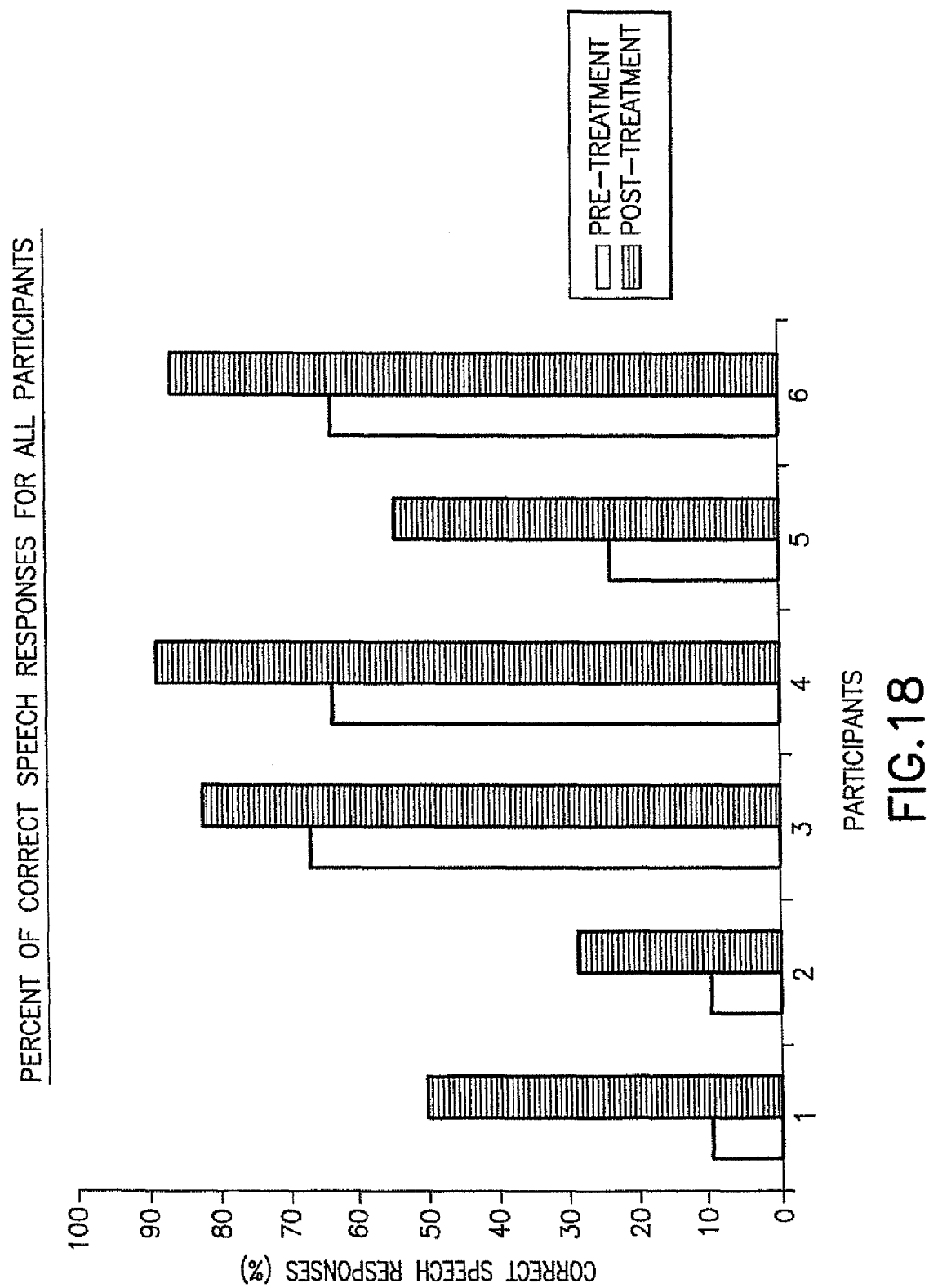
FIG. 18 shows a summary and comparison of the percent correct speech responses for all the Participants, before and after the treatment sessions.

FIG. 18 shows the percent of correct speech responses for all the Participants prior to the first treatment session and after the treatment sessions as discussed hereinbefore. FIG. 18 demonstrates that there are significant increases in the percent of correct speech responses for diverse speech impairments secondary to different types of cerebral palsy in diverse children and adolescents.

In those Examples where the participant had a foreign language early childhood and to some extent a foreign language home environment, namely Participants 3 and 4, the English language speech impairments were nonetheless significantly diminished by the psychostimulant treatment pursuant to the present invention.

The improvements according to the present invention are variously measured by the improvement in correct imitations or pronunciations as to intelligible words and the improvement in speech-language equivalent age, and may also be measured by the rate of acquisition of speech-language capability or functionality. The Figures demonstrate these several improvements.

Anecdotal evidence, particularly by the parents or guardians of the Participants, demonstrates that the speech and language improvements, in turn, effected improvements in and retention of socialization skills and emotional well being. The literature suggests that improvements in speech and language functionality correlate with an increase in survival skills and longevity.

A repeated T-test was utilized as a statistical analysis of the difference in speech-language ability before and after treatment; and with respect to the percent responses p=0.0214, and speech-language age equivalence p=0.0235.

A broad range of psychostimulants are contemplated by the present invention, and include the NDRIs and amphetamines. Preferred psychostimulants include, by way of example, Adderall® (dextroamphetamine plus amphetamine); atomoxetin (Strattere®); caffeine (Nodoz®, Vivarin®); dextroamphetamine (Dexedrine®); guanfacine (INTUNIV®) extended-release tablets; methylphenidate (Concerta®; Metadata®ER; Metadate® CD); pemoline (Cylert®); phentermine (Fastin®, Lonamin®); armodafinil- (NUVIGIL®); benzphetamine (Didrex®); dexmethylphenidate (Foaclin®); diethyipropionate (Tenuate®); lisdexamfetamine dimestylate (Vyvanse®); modafinil (Provigil®); phendimetrizine (Bontril SR®, Prelu-2®); and sibutramine (Meridia®). One preferred NDRI is Methylphenidate®; and one preferred amphetamine is Dexedrine®.

Particularly suitable psychostimulants pursuant to the present invention further include the norephinephrine-dopamine reuptake inhibitors (NDRIs) including, by way of example, methylphenidate, modafinil, armodafiml and dexmethylphenidiate, as discussed in co-pending application PCT/US2012/038312, filed May 17, 2012, incorporated herein by reference thereto. Extended release, controlled release and immediate release forms methylphenidate are contemplated as useful psychostimulants. Immediate release methylphenidate is a preferred psychostimulant.

It is also within the contemplation of the present invention to provide a dosage regimen starting with an initial dose of at least about 2.5 mg and increasing the dosage within the same day or in a subsequent day, which increase in dosages would be commensurate with the continuing increase in speech-language age equivalence, particularly where the differential between chronological age and speech-language equivalence age is substantial prior to treatment.

The foregoing demonstrates that modest dosages of 2.5 to 10 mg/day of a psychostimulant result in an increase in the percentage of correctly pronounced intelligible syllables or words. The percentage increase in the correctly produced sounds, syllables, words or language is generally at least about 20 percent and upwards of several hundred percent in some cases. The foregoing further demonstrates that the increase in correctly pronounced syllables or words persists over time even after the psychostimulant is no longer efficaciously active or present in the body.

In the art related to the treatment of hyperactivity in children, particularly including ADD and ADHD, it is established practice to administer methylphenidate. Psychosocial behavioral disorders such as lack of attentiveness and verbal regression are improved with the administration of methylphenidate, as disclosed in U.S. Pat. No. 6,121,261, issued Sep. 19, 2006 to Glatt et al; and Creager et al., Journal of Speech and Hearing Research, 623-628 (1967). Methylphenidate is administered daily to children suffering psychobehavioral and neuropsychological disorders. The behavioral improvement is short lived, and lasts, at most, several hours after administration of the methylphenidate. Unless such daily dosages are maintained, the subject reverts to his or her attention deficits and hyperactivity.

Intensive speech-language therapy sessions over several weeks, as discussed hereinbefore in par. [0009], reports an improvement of at best about 14% to 16% in the number of correctly pronounced single or multiple words, whereas in a single psychostimulant administration pursuant to the present invention, particularly with respect to Participant 1, there was an about 250% increase in the number of correctly imitated or pronounced syllables or words. (See FIG. 3, Session 1).

The foregoing demonstrates persistent diminishment of the cerebral palsy impaired speech and language, and suggests that alternate neural pathways are being effected. These alternate route neural pathways seemingly persist even where the psychostimulant is no longer efficaciously active or present in the body.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the subject being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method for evaluating a subject for a psychostimulant having antidepressant or mood-elevating properties treatment of a speech impairment secondary to cerebral palsy, said method comprises:
   (a) diagnosing the subject as having cerebral palsy;
   (b) determining the subject has a speech impairment secondary to cerebral palsy;
   (c) determining the subject has a threshold cognitive capacity; and
   wherein when the subject has cerebral palsy impaired speech and the threshold cognitive capacity, the subject is a candidate for administration of the psychostimulant to diminish the speech impairment.

2. The method of claim 1, wherein step (c) further comprises determining the cognitive age of the subject, and the chronological age is greater than the cognitive age.

3. The method of claim 1, wherein the threshold cognitive capacity is at least about that of a 2 year old.

4. The method of claim 1, wherein step (b) further comprises measuring the speech-language age equivalence of the subject, and wherein when the chronological age of the subject is greater than the speech-language age equivalence of the subject.

5. The method of claim 1, wherein step (a) further comprises determining that the subject has a substantially intact frontal lobe.

6. The method of claim 5, wherein step (a) further comprises determining that the subject has a damaged portion of the brain, and an undamaged portion extending from the substantially intact frontal lobe to the auditory cortex.

7. The method of claim 1, wherein step (a) further comprises conducting a brain scan and determining that the subject has a substantially intact frontal lobe, a damaged portion, and an undamaged portion extending from the substantially intact frontal lobe to the auditory cortex.

8. The method of claim 1, wherein step (a) further comprises analyzing a brain scan of the subject.

9. The method of claim 1, wherein step (c) further comprises:
   (i) determining that the subject is following two-step related commands; and
   (ii) in a verbal subject, determining that the subject is using basic two-word combinations; and
   (iii) in a non-verbal subject, determining that the subject is:
      (A) sequencing limited vocalizations; and
      (B) moving the body to a rhythm when modeled.

10. The method of claim 9, wherein the speech impairment secondary to cerebral palsy comprises dysarthric speech.

11. The method of claim 10, wherein the dysarthric speech comprises non-bilabial speech.

12. The method of claim 1, further comprising (d) administering the psychostimulant to the subject.

13. The method of claim 12, wherein the psychostimulant comprises mood-altering or antidepressant properties affecting neural pathways to effect accessing vocabulary and correctly pronouncing words and syllables.

14. The method of claim 3, wherein the subject is a child or adolescent.

15. The method of claim 10, wherein the subject is a child or adolescent.

16. The method of claim 13, wherein the subject is a child or adolescent.

17. A method for evaluating a subject for a psychostimulant having antidepressant or mood-elevating properties treatment of a speech impairment secondary to cerebral palsy, said method comprises:
   (a) diagnosing the subject as having cerebral palsy;
   (b) determining the subject has a speech impairment secondary to the cerebral palsy;
   (c) determining the subject has a threshold cognitive capacity;
   and wherein step (c) further comprises determining the cognitive age of the subject, and wherein the chronological age is greater than the cognitive age, and wherein the threshold cognitive capacity is at least about a 2 year old, and wherein step (b) further comprises measuring the speech-language age equivalence of the subject; and wherein when the chronological age of the subject is greater than the speech-language age equivalence of the subject, the subject is evaluated for administration of the psychostimulant to diminish the speech impairment.

18. The method of claim 17, wherein step (c) comprises:
   (i) determining that the subject is following two-step related commands; and
   (ii) in a verbal subject, determining that the subject is using basic two-word combinations; and
   (iii) in a non-verbal subject, determining that the subject is:
      (A) sequencing limited vocalizations; and
      (B) moving the body to a rhythm when modeled.

19. The method of claim 18, wherein the subject is a child or adolescent.

20. The method of claim 1, wherein the subject is a participant in a clinical trial.

21. The method of claim 17, wherein the subject is a participant in a clinical trial.

22. The method of claim 1, wherein the subject is a child or adolescent and the speech impairment comprises severe dysarthric speech, and the child or adolescent has no or limited bilabial functionality.

23. The method of claim 1, wherein the psychostimulant comprises an NDRI.

24. The method of claim 23, wherein the NDRI comprises a methylphenidate.

* * * * *